US012788953B2

(12) United States Patent
Prasad et al.

(10) Patent No.: US 12,788,953 B2
(45) Date of Patent: Nov. 10, 2026

(54) SKIN PREPARATION APPLICATOR

(71) Applicant: Becton, Dickinson and Company, Franklin Lakes, NJ (US)

(72) Inventors: Shishir Prasad, Ramsey, NJ (US); Balaji Kannan, Chennai (IN); Mukilan Balamurugan, Theni (IN); Edwin Jeyaseelan Arockia Doss, Madurai (IN)

(73) Assignee: Becton, Dickinson and Company, Franklin Lakes, NJ (US)

( * ) Notice: Subject to any disclaimer, the term of this patent is extended or adjusted under 35 U.S.C. 154(b) by 836 days.

(21) Appl. No.: 18/094,890

(22) Filed: Jan. 9, 2023

(65) Prior Publication Data

US 2024/0226349 A1 Jul. 11, 2024

(51) Int. Cl.
*A61M 35/00* (2006.01)
*A61B 5/15* (2006.01)

(52) U.S. Cl.
CPC ....... *A61M 35/003* (2013.01); *A61B 5/15003* (2013.01); *A61B 5/150351* (2013.01)

(58) Field of Classification Search
CPC ........ A61M 35/003; A61M 2037/0007; A61M 35/00; A61M 35/006; A61H 2201/105; A61H 15/0092; A61H 15/00; A61H 2015/0064; A61H 2015/0007; A61H 2015/0042; A45D 34/041; A45D 34/04; A45D 40/261; A45D 40/26
See application file for complete search history.

(56) References Cited

U.S. PATENT DOCUMENTS 2,807,817 A * 10/1957 Ackerman ........... A45D 34/041 401/213
3,235,900 A * 2/1966 Klassen ............... A45D 34/041 401/175
4,342,522 A * 8/1982 Mackles ............. A45D 34/041 401/214
4,799,926 A * 1/1989 Haber ..................... A61M 5/31 604/199
5,435,660 A 7/1995 Wirt
5,553,957 A * 9/1996 Dornbusch .......... A45D 34/041 401/209
6,264,619 B1 * 7/2001 Ferguson ......... A61B 5/150305 206/569
8,956,065 B2 2/2015 Froimson
9,016,967 B2 4/2015 Law et al.
2003/0007826 A1 * 1/2003 Badejo ................ A61M 35/003 401/209
2006/0072962 A1 4/2006 Cybulski et al.
(Continued)

FOREIGN PATENT DOCUMENTS

CN 109224279 A 1/2019
CN 212698882 U 3/2021
WO 2007144792 A1 12/2007

*Primary Examiner* — Sarah Al Hashimi
*Assistant Examiner* — Seth Han
(74) *Attorney, Agent, or Firm* — Servilla Whitney LLC

(57) ABSTRACT

Provided herein is a skin preparation device having a container having a proximal end, a distal end, and a sidewall therebetween, defining an interior, a disinfecting solution received within the interior, and an applicator arranged at the distal end of the container, the applicator in fluid communication with the interior of the container.

19 Claims, 33 Drawing Sheets

(56) References Cited

U.S. PATENT DOCUMENTS

| | | | | |
|---|---|---|---|---|
| 2008/0003052 | A1* | 1/2008 | Lee | A61M 35/003 401/209 |
| 2009/0099529 | A1* | 4/2009 | Anderson | A61M 39/20 604/192 |
| 2015/0126944 | A1* | 5/2015 | Stemer | A61M 35/003 604/290 |
| 2017/0136804 | A1 | 5/2017 | Orem et al. | |
| 2018/0242709 | A1 | 8/2018 | Herzmann | |

* cited by examiner

SKIN PREPARATION APPLICATOR

BACKGROUND OF THE INVENTION

Field of the Invention

The present disclosure relates generally to devices, systems, and kits for preparing skin for medical procedures.

Description of Related Art

When medical procedures that involve a patient's skin are employed, it is typical to prepare the skin for the procedure. For example, venipuncture requires piercing the skin, and external microbes, such as those normally present on the skin, can inadvertently be introduced into the body, raising the possibility of infection.

Various disinfecting solutions for skin preparation are known, such as chlorhexidine gluconate (CHG) and isopropyl alcohol (IPA). A medical professional performing skin preparation typically estimates a volume of preparation to use (e.g., a volume of disinfecting solution), leading to issues such as not enough disinfecting solution or excessive disinfecting solution, causing tackiness in the work area and/or longer drying time. Inconsistent dispensing rate of disinfecting solution may lead to inconsistent scrubbing that is stopped too early for effective preparation.

Accordingly, there is a need in the field for new devices that provide accurate amounts of disinfecting solutions and allow for medical professionals to provide adequate skin preparation for medical procedures.

SUMMARY OF THE INVENTION

Provided herein is a skin preparation device having a container having a proximal end, a distal end, and a sidewall therebetween defining an interior, a disinfecting solution received within the interior, and an applicator arranged at the distal end of the container, the applicator in fluid communication with the interior of the container.

In accordance with an embodiment of the present invention, the applicator includes an axially displaceable roller applicator.

In accordance with an embodiment of the present invention, the applicator includes a porous material.

In accordance with an embodiment of the present invention, the applicator includes a ring of a porous material defining a central opening and arranged circumferentially about the distal end of the container, and a roller applicator received in the central opening of the porous material.

In accordance with an embodiment of the present invention, the roller applicator includes a spherical member received rotatably within the distal end of the container.

In accordance with an embodiment of the present invention, the distal end of the container includes an enclosure in which the spherical member is received.

In accordance with an embodiment of the present invention, the enclosure includes an open distal end such that at least a portion of the spherical member extends distally beyond the enclosure.

In accordance with an embodiment of the present invention, the spherical member is held within the enclosure by an inwardly-extending flange.

In accordance with an embodiment of the present invention, the enclosure is a cylindrical enclosure having a frustoconical distal end.

In accordance with an embodiment of the present invention, the enclosure includes one or more openings in a proximal end thereof, the one or more openings placing the spherical member in fluid communication with the interior of the container.

In accordance with an embodiment of the present invention, the one or more openings includes a plurality of circular openings.

In accordance with an embodiment of the present invention, the one or more openings includes a plurality of elongated slots.

In accordance with an embodiment of the present invention, the plurality of slots are arranged in a radially-extending pattern from a center of the proximal end of the enclosure to an outer edge of the proximal end of the enclosure.

In accordance with an embodiment of the present invention, the plurality of elongated slots intersect at a center of the proximal end of the enclosure.

In accordance with an embodiment of the present invention, the plurality of elongated slots extend distally from a proximal end of the enclosure.

In accordance with an embodiment of the present invention, the applicator includes a spherical member comprising one or more indentations in an outer surface thereof.

In accordance with an embodiment of the present invention, the one or more indentations includes a plurality of circular indentations.

In accordance with an embodiment of the present invention, the one or more indentations includes a plurality of elongated indentations.

In accordance with an embodiment of the present invention, the distal end of the container is rotatable between a first configuration, in which the applicator is not in fluid communication with the interior of the container, and a second configuration, in which the applicator is in fluid communication with the interior of the container.

In accordance with an embodiment of the present invention, the skin preparation device further includes a removable film arranged on an outer surface of the applicator.

In accordance with an embodiment of the present invention, the skin preparation device further includes a cap removably attached to the distal end of the container.

In accordance with an embodiment of the present invention, the disinfecting solution includes chlorhexidine gluconate (CHG).

In accordance with an embodiment of the present invention, the disinfecting solution includes isopropyl alcohol (IPA).

In accordance with an embodiment of the present invention, the disinfecting solution includes from about 0.5% to about 4% CHG and about 70% IPA.

In accordance with an embodiment of the present invention, the disinfecting solution includes about 2% CHG and about 70% IPA.

In accordance with an embodiment of the present invention, a kit includes a blood collection device having a catheter assembly having a catheter and a fluid flow conduit in fluid communication with the catheter, a blood collection device holder, and a skin preparation device removably received at least partially within the blood collection device holder.

In accordance with an embodiment of the present invention, a kit includes a drug delivery device, and a skin preparation device received at least partially within the drug delivery device.

DESCRIPTION OF THE INVENTION

Figure 1B:
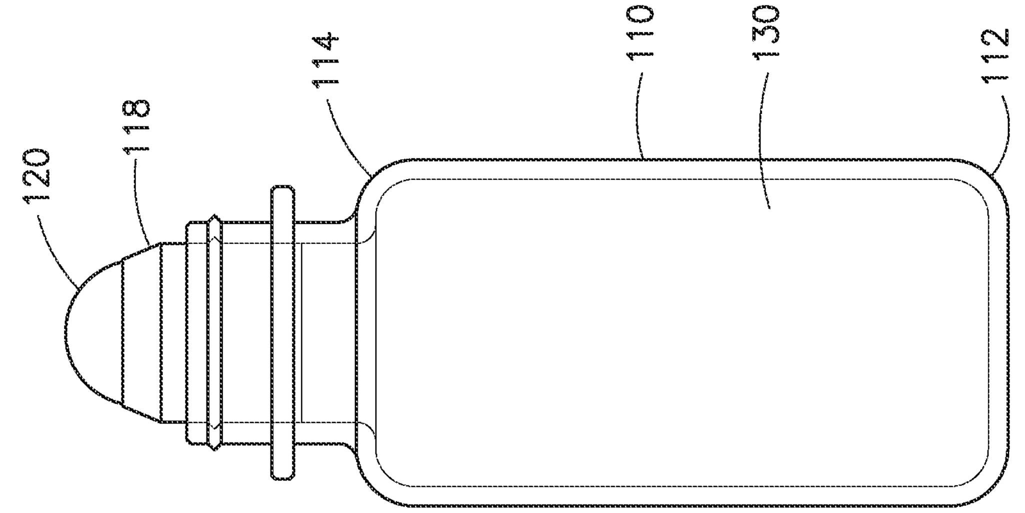
FIG. 1B is a side view of a skin preparation device according to non-limiting embodiments described herein.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

It should be understood that any numerical range recited herein is intended to include all values and sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10.

Provided herein are devices, systems, and kits for skin preparation associated with medical procedures, such as drug delivery and venipuncture, wherein skin preparation, for example with a disinfecting solution, is advantageous for limiting risk of infection.

Figure 1A:
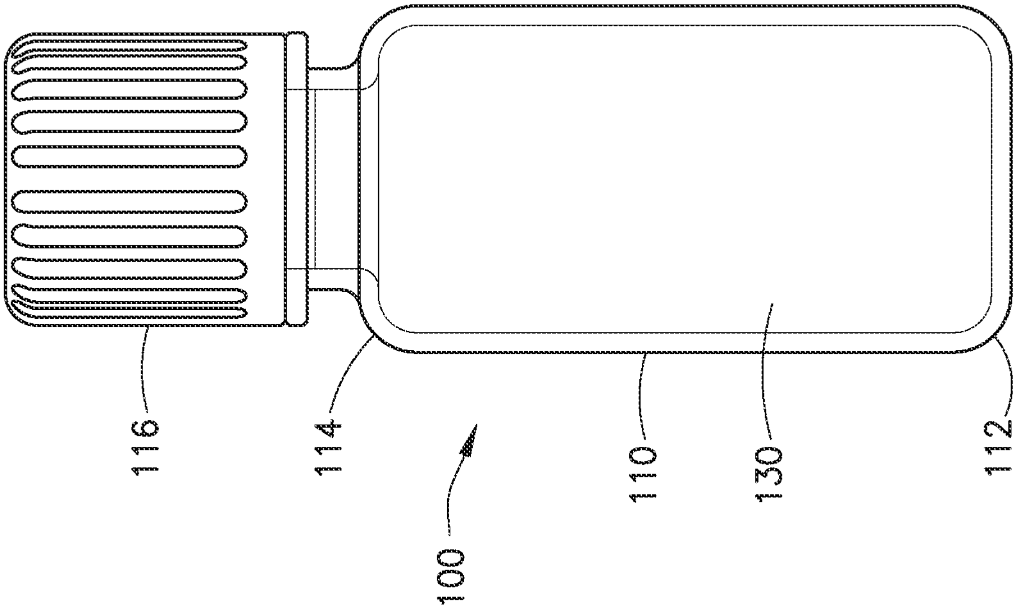
FIG. 1A is a side view of a skin preparation device according to non-limiting embodiments described herein.
Figure 2:
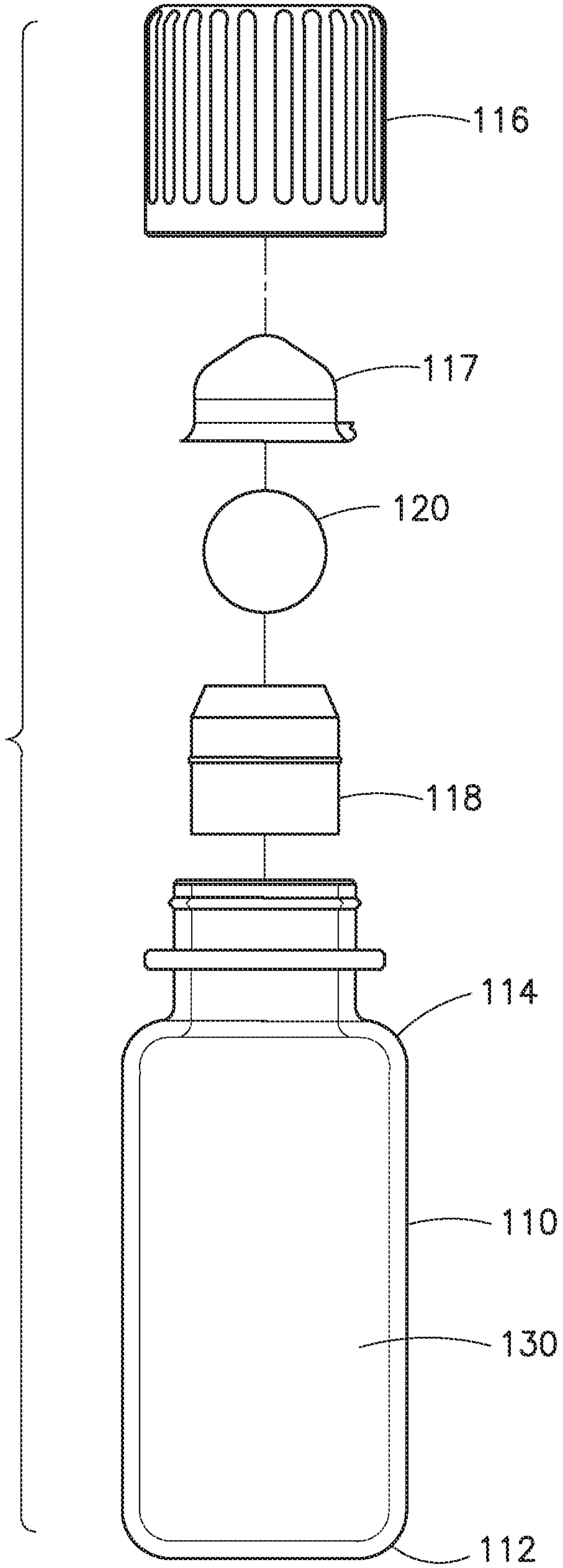
FIG. 2 is an exploded perspective view of a skin preparation device according to non-limiting embodiments described herein.
Figure 9:
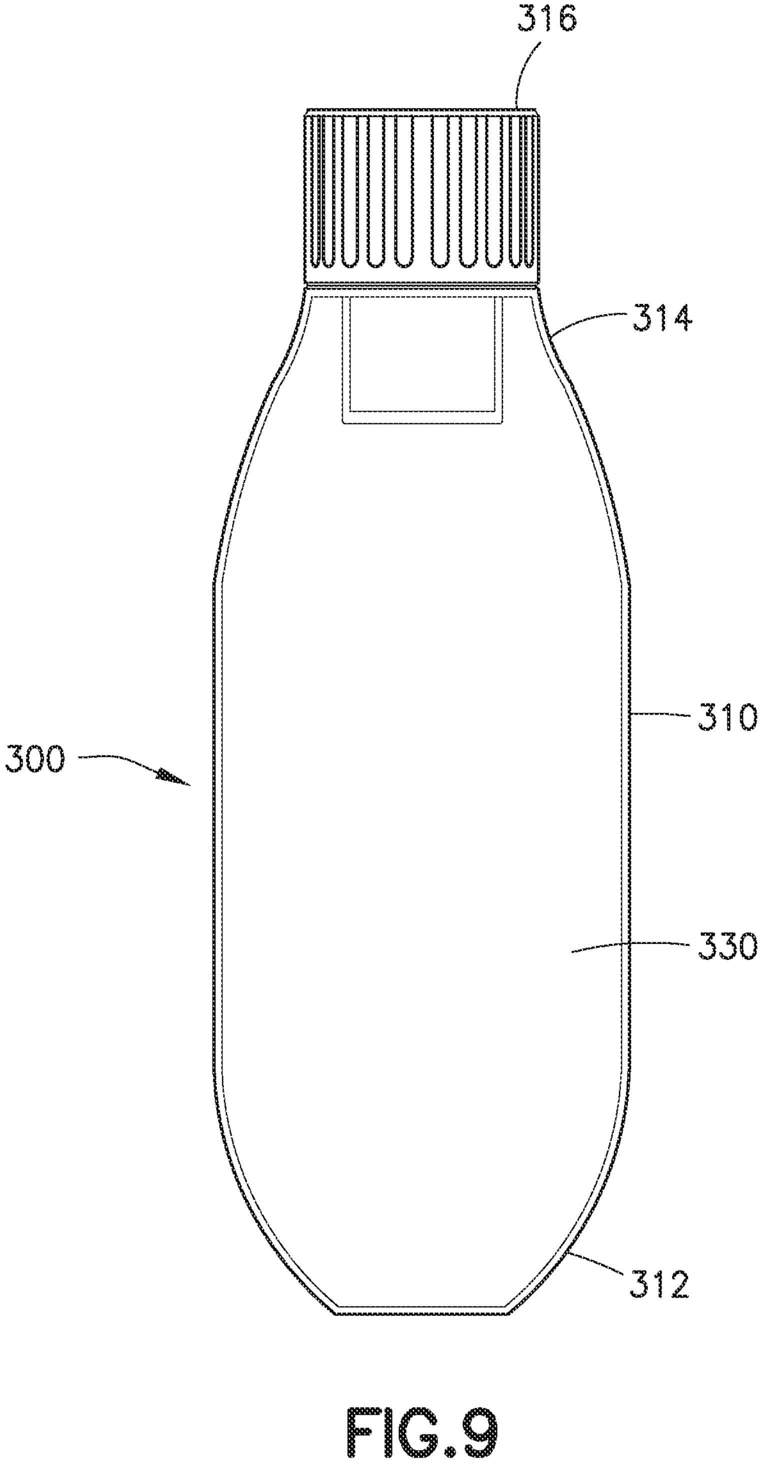
FIG. 9 is a side view of a skin preparation device according to non-limiting embodiments described herein.
Figure 10A:
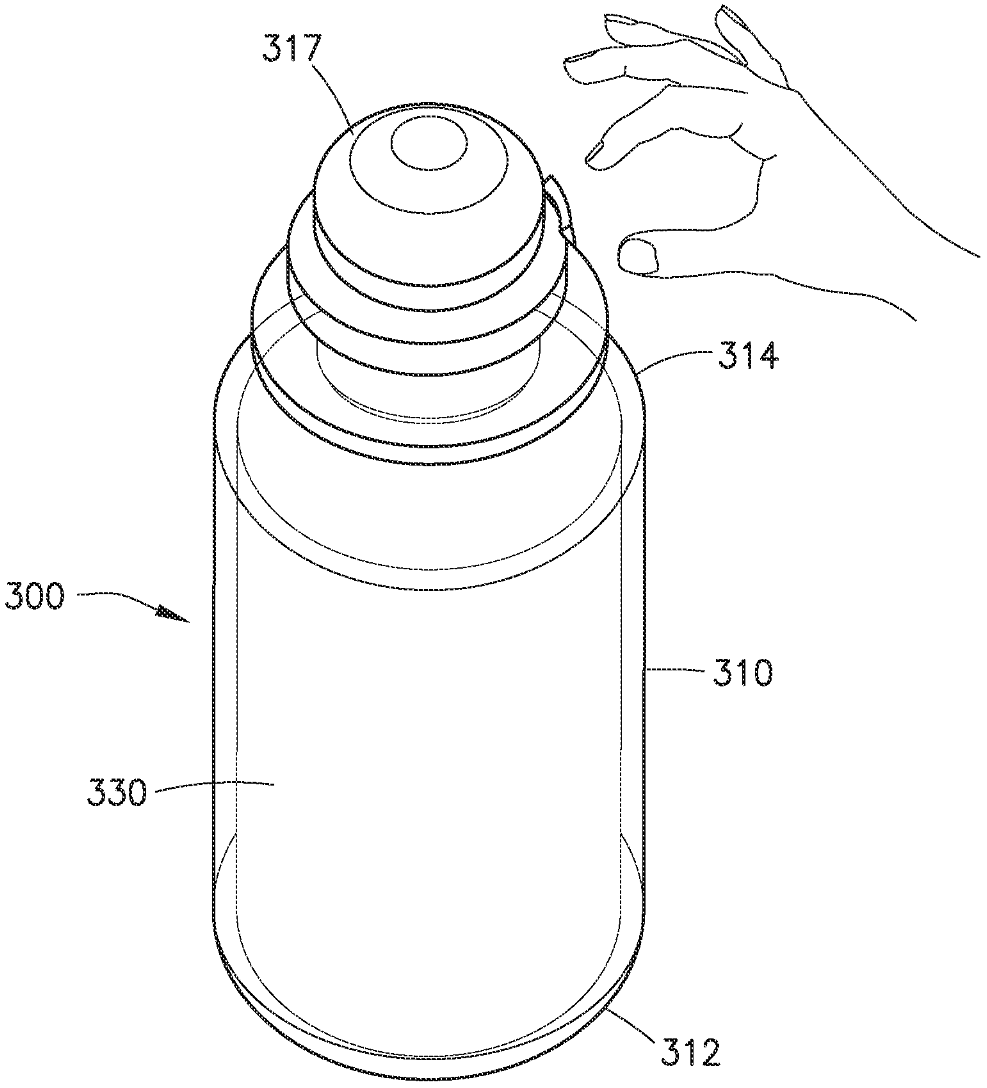
FIG. 10A is a perspective view of a skin preparation device according to non-limiting embodiments described herein.
Figure 10B:
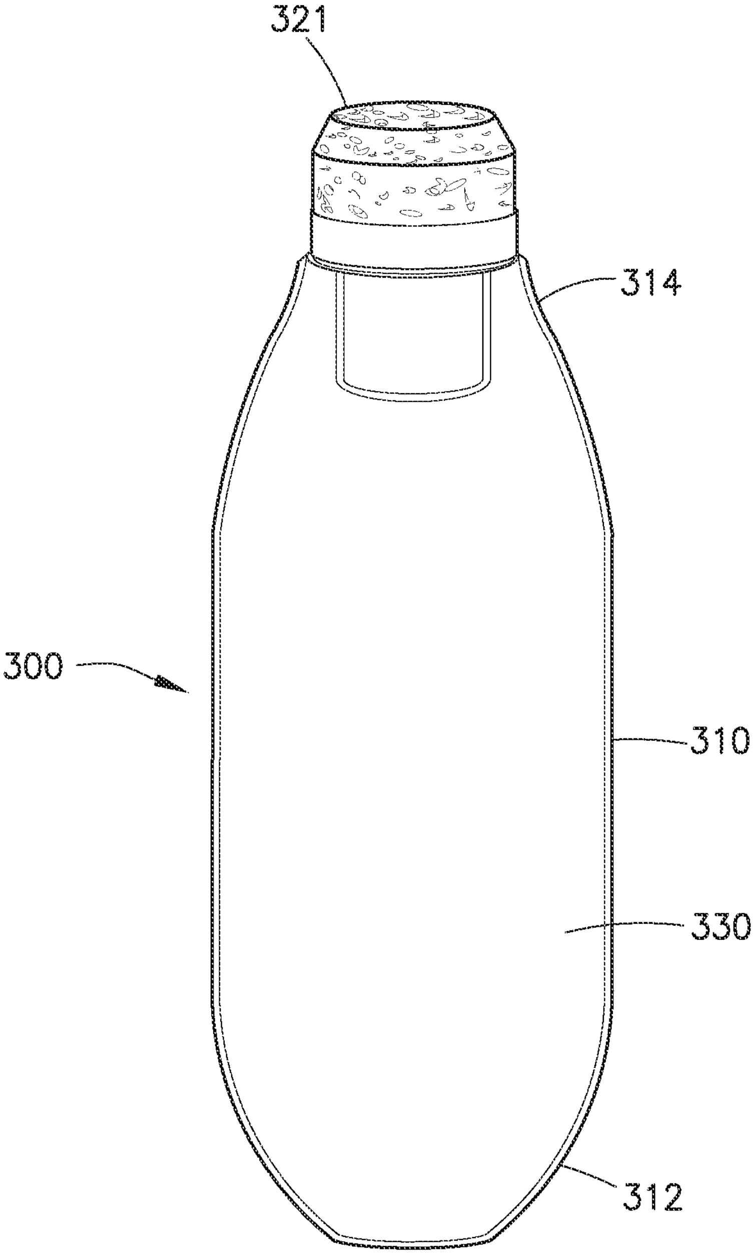
FIG. 10B is a perspective view of a skin preparation device according to non-limiting embodiments described herein.
Figure 11A:
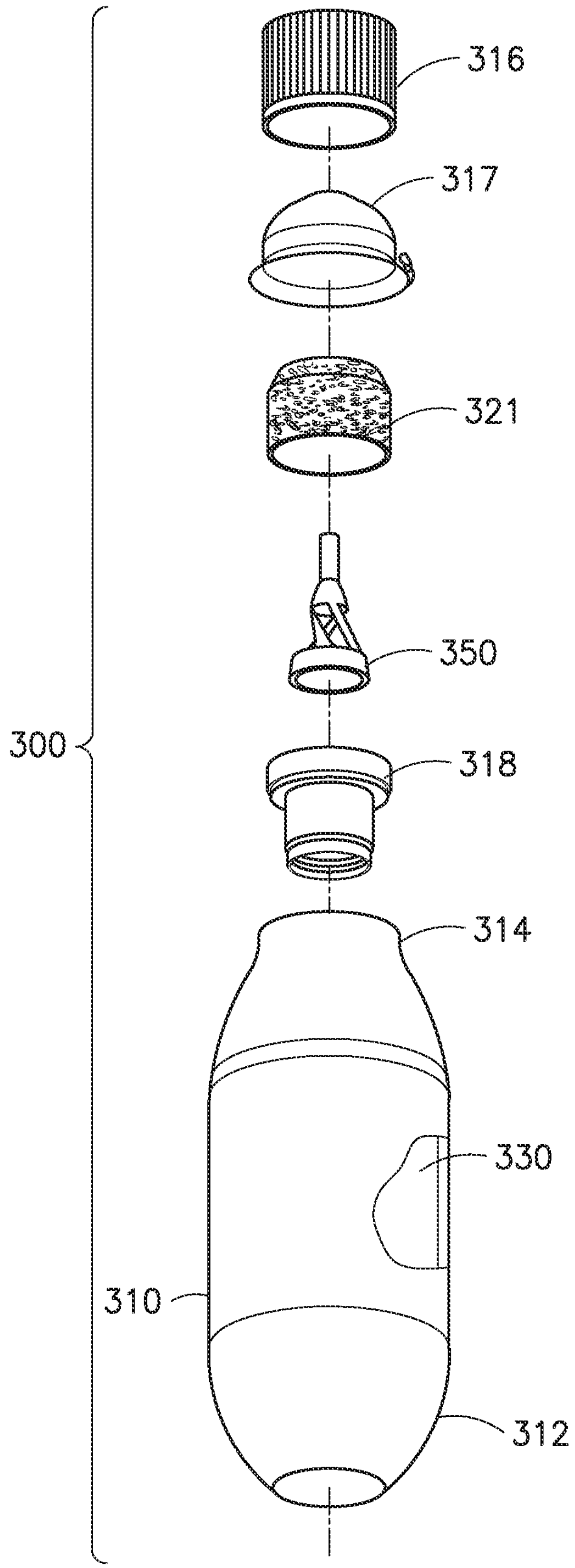
FIG. 11A is an exploded view of skin preparation devices according to non-limiting embodiments described herein.
Figure 11B:
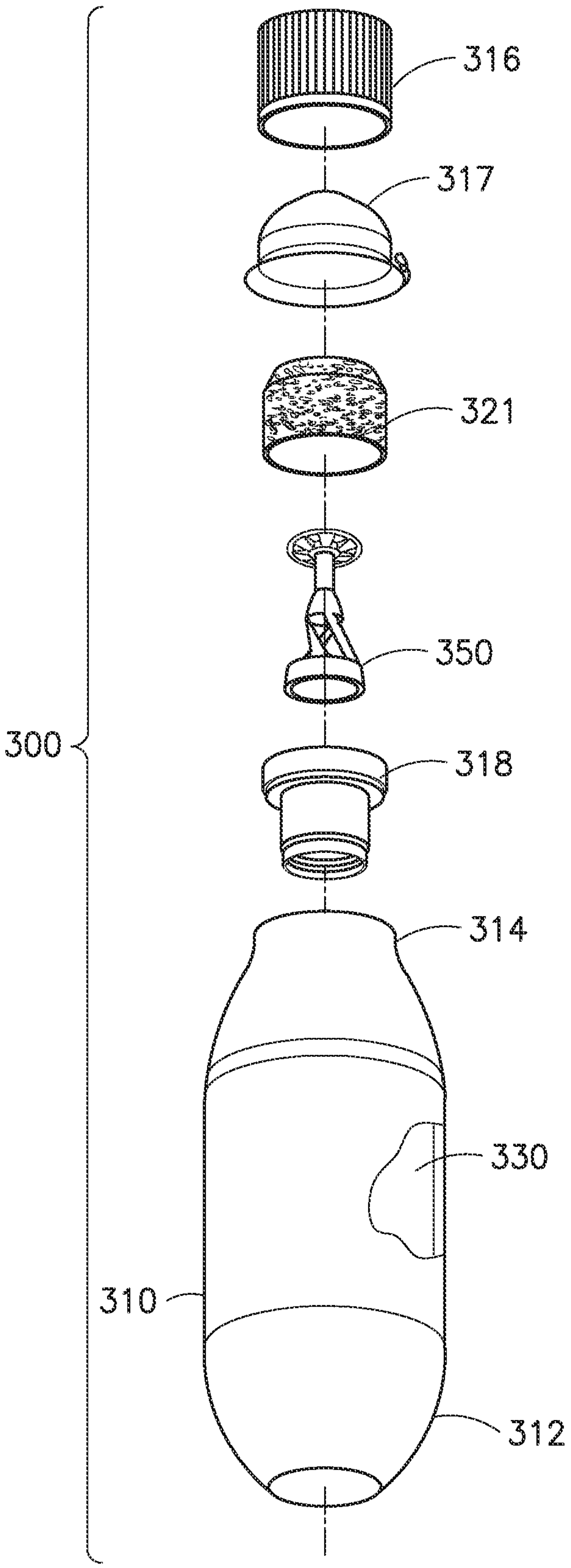
FIG. 11B is an exploded view of skin preparation devices according to non-limiting embodiments described herein.
Figure 12:
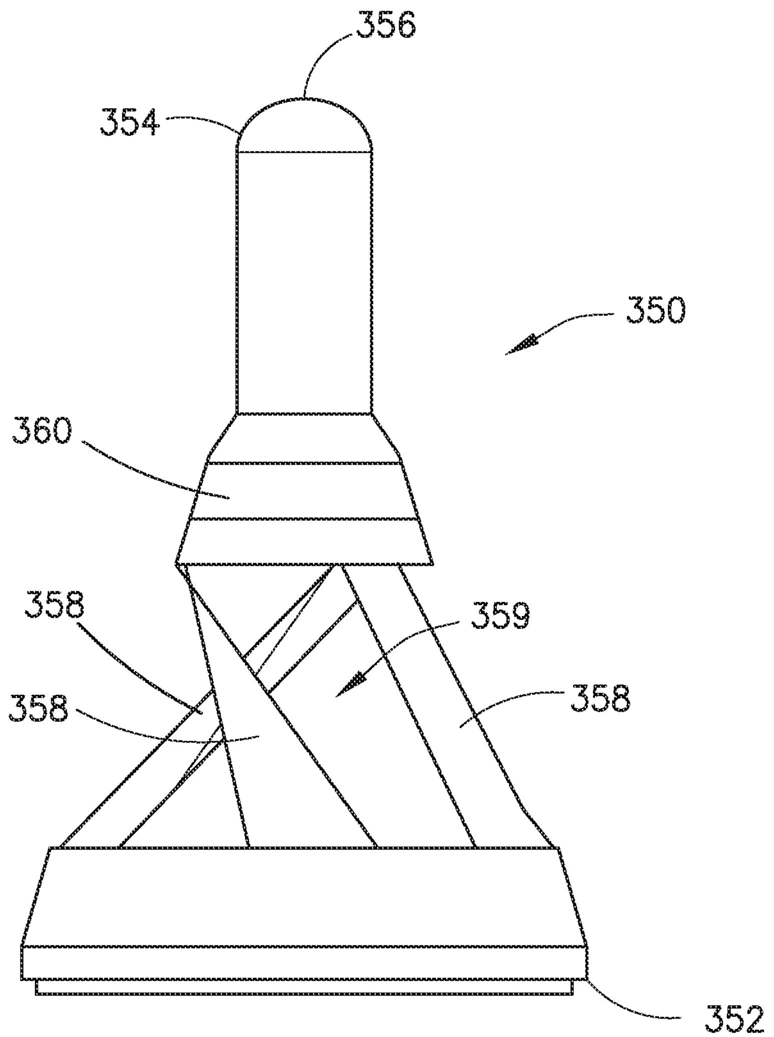
FIG. 12 is a component of a skin preparation device according to non-limiting embodiments described herein.

Turning to FIGS. 1A-2, shown is a non-limiting embodiment of a skin preparation device 100. Device 100 includes a container 110, having a proximal end 112 and a distal end 114, defining an interior 130 configured to hold a liquid, for example a disinfecting solution. Suitable skin disinfecting solutions are known to those of skill in the art, and may include, for example, chlorhexidine gluconate (CHG) and alcohols, such as isopropyl alcohol (IPA). In non-limiting embodiments, the disinfecting solution includes about 0.5% to about 4% CHG, optionally, about 2% CHG, and/or about 70% IPA. In non-limiting embodiments, the disinfecting solution includes about 2% CHG and about 70% IPA. Returning to the structure of device 100, container 110 may be formed of any useful material, such as plastics or glass, may be opaque, at least partially opaque, at least partially translucent, translucent, at least partially transparent, and/or transparent, and may assume any useful shape and configuration, including an elongated cylindrical shape as shown in FIGS. 1A, 1B, and 11, a tapered shape as shown in FIG. 9, and a compact cylindrical shape as shown in FIGS. 16A-16B. Device 100 may include a cap 116, as shown in FIG. 1A, and cap 116 may be removably connectable to container 110, for example through a threaded connection or press fit at distal end 114 of container 110. Container 110 may have one or more labels arranged thereon, for example identifying the contents held therein.

With continuing reference to FIGS. 1A-2, device 100 includes an applicator 120 configured to aid in the delivery of disinfecting solution to the skin of a patient. In the non-limiting embodiment of FIGS. 1A-2, applicator 120 is a spherical member, such as a roller applicator, and may be received rotatably within distal end 114 of container 110. Applicator 120 may be formed of any suitable material, for example plastic(s), elastomer(s), metal(s), glass, and the like. In non-limiting embodiments that will be discussed later, applicator 120 may be a combination of a spherical member and a porous member, such as a foam member. Applicator 120 may be in fluid communication, optionally reversibly so, with interior 130 of container 110, and thus the disinfecting solution held therein. Disinfecting solution may be applied to the skin through applicator 120 based on, for example, gravity, capillary action, Bernoulli's principle, and/or surface tension.

Figure 3B:
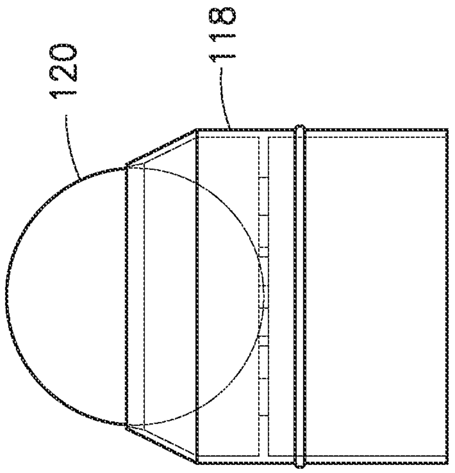
FIG. 3B is a side view of a skin preparation device according to non-limiting embodiments described herein.
Figure 3A:
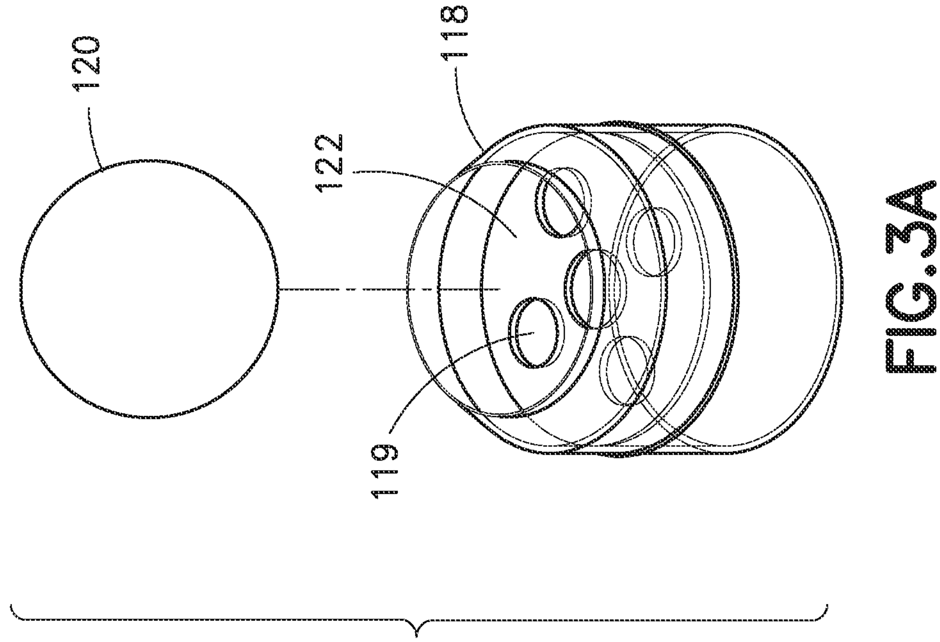
FIG. 3A is an exploded view of a skin preparation device according to non-limiting embodiments described herein.
Figure 4A:
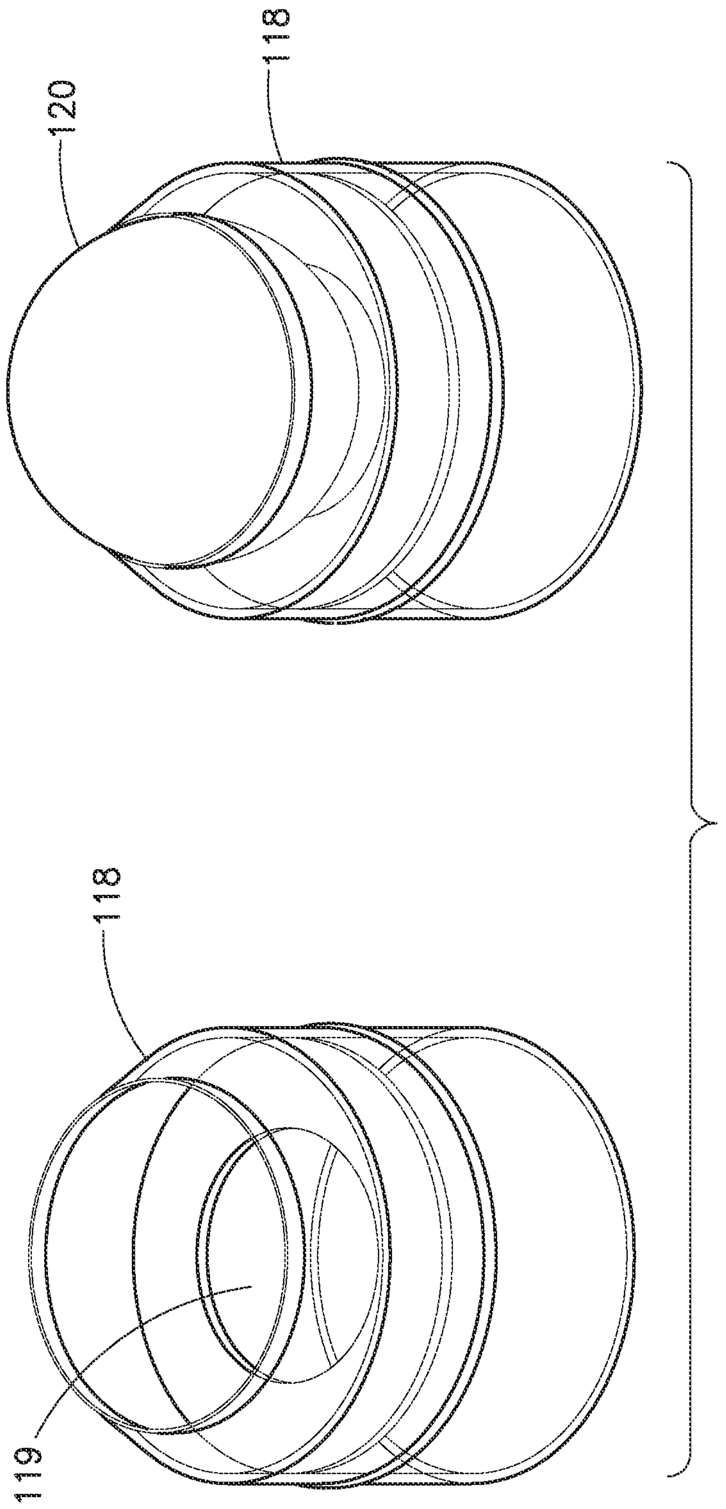
FIG. 4A is a partial view of skin preparation devices according to non-limiting embodiments described herein.
Figure 4B:
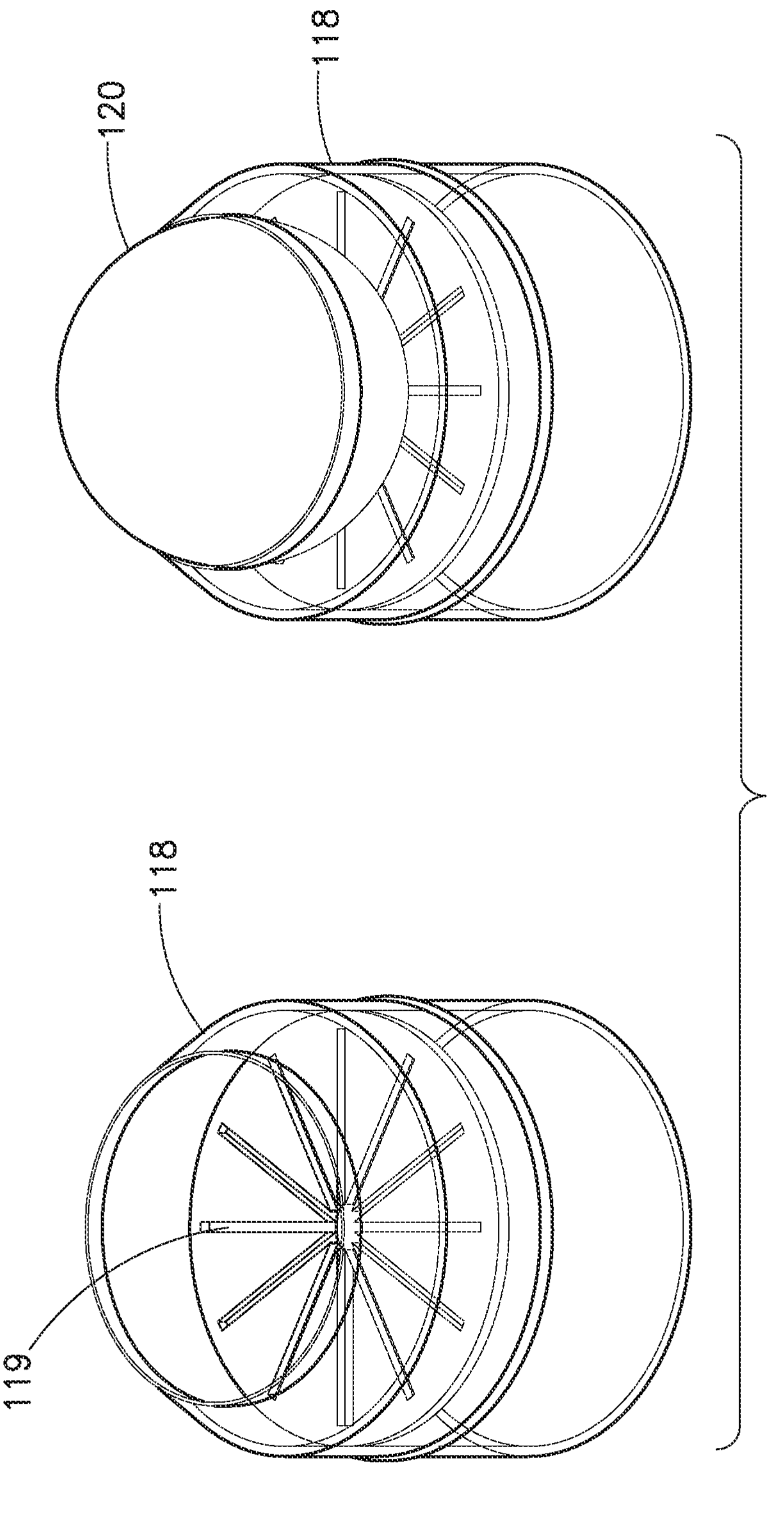
FIG. 4B is a partial view of skin preparation devices according to non-limiting embodiments described herein.
Figure 4C:
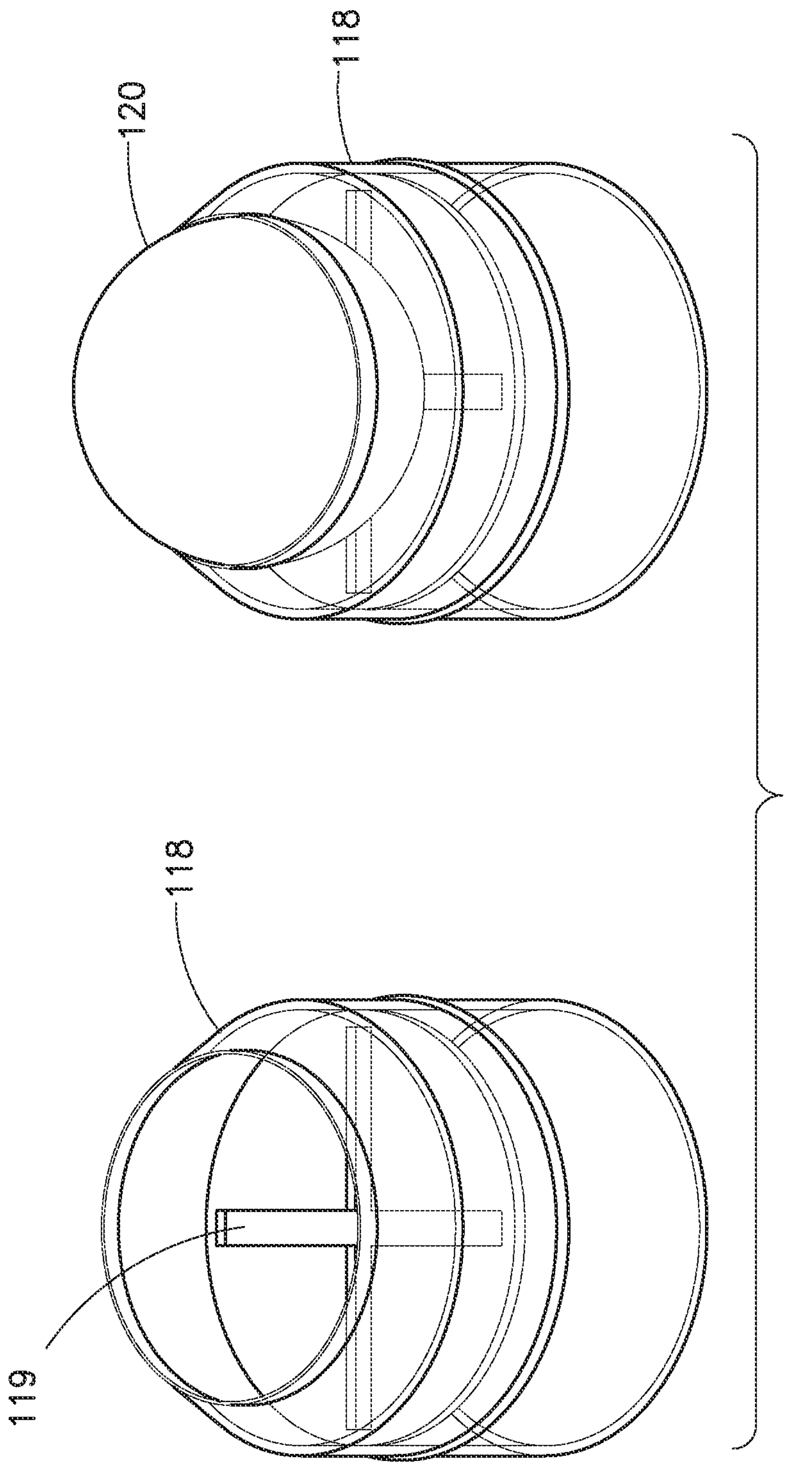
FIG. 4C is a partial view of skin preparation devices according to non-limiting embodiments described herein.
Figure 4D:
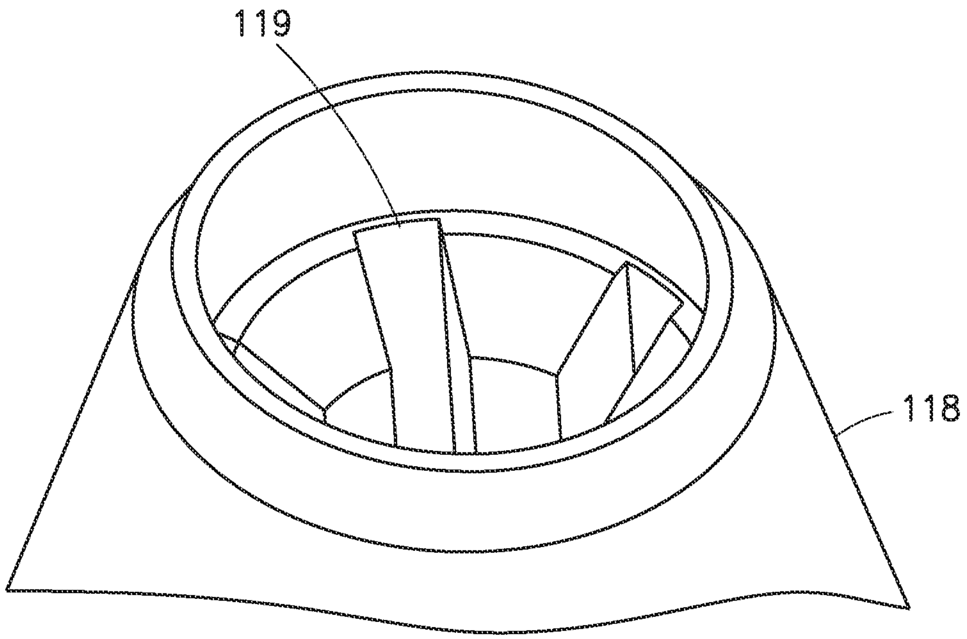
FIG. 4D is a partial view of skin preparation devices according to non-limiting embodiments described herein.

In non-limiting embodiments, applicator 120 is received within an enclosure 118, which may define a socket arranged at distal end 114 of container 110. In non-limiting embodiments, for example as shown in FIGS. 3A-3B, enclosure 118 may be substantially cylindrical, optionally with a frustoconical distal portion having an opening, such that at least a portion of applicator 120, which may be received at least partially within enclosure 118 (e.g., within a socket formed by enclosure 118) extends distally beyond enclosure 118. In non-limiting embodiments, applicator 120 is axially displaceable within enclosure 118 and/or distal end 114 of container 110, such that device 100 can be pressed onto the patient's skin during preparation, forming one or more fluid paths between an outer surface of applicator 120 and enclosure 118 and/or distal end 114 of container 110 to allow for an increased amount of disinfecting solution to be dispensed. In non-limiting embodiments, enclosure 118 may include a flexible web 122 at a proximal end thereof, which can flex as a user applies pressure to skin, axially displacing applicator 120 proximally. Flexible web 122 may be resilient, such that as force is removed, web 122 returns to an original position, moving applicator 120 axially in a distal direction.

Figure 6A:
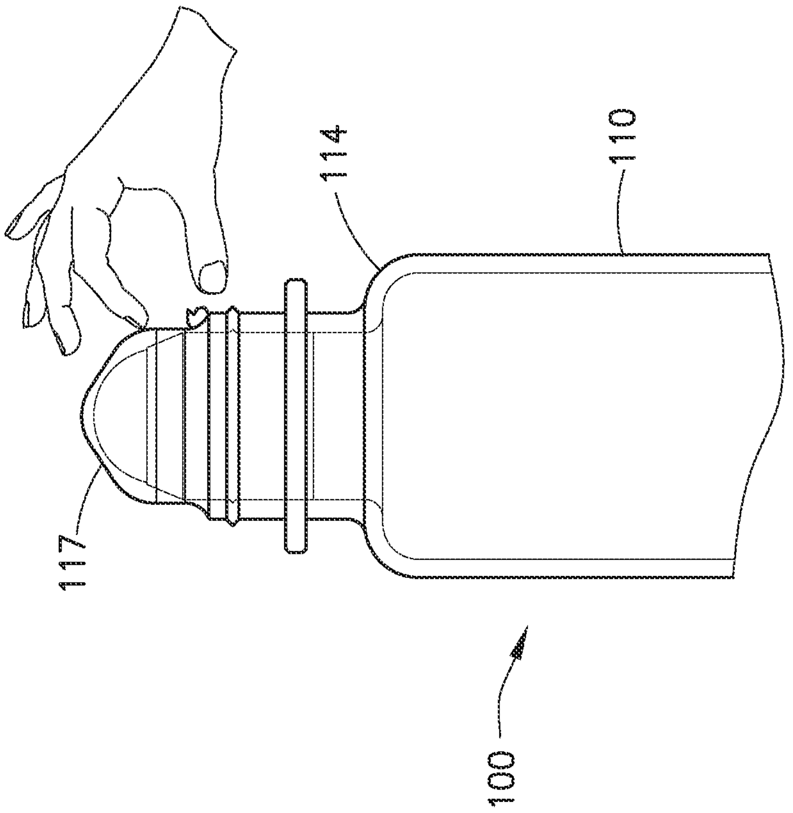
FIG. 6A is a side view of a skin preparation device according to non-limiting embodiments described herein.
Figure 6B:
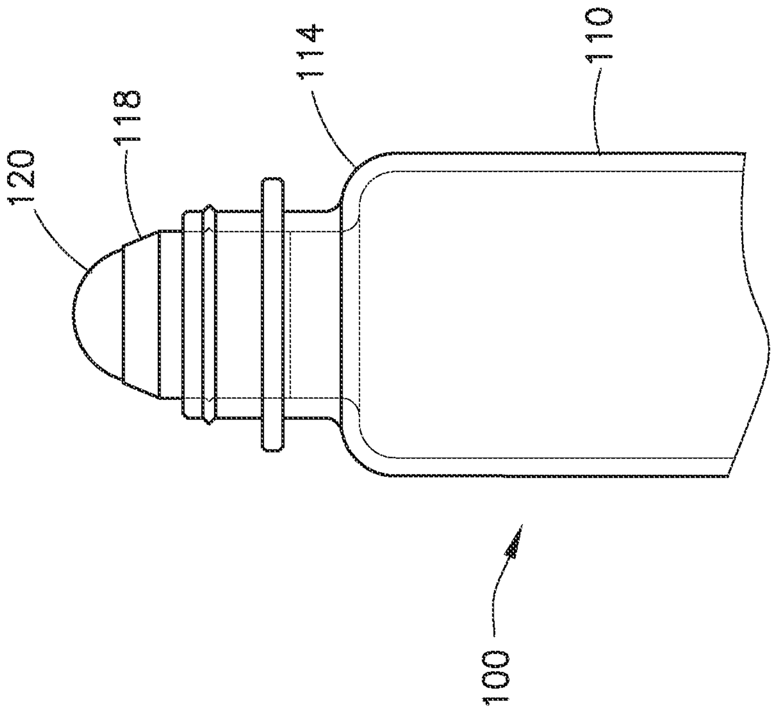
FIG. 6B is a side view of a skin preparation device according to non-limiting embodiments described herein.

With continuing reference to FIG. 2 and FIGS. 6A-6B, in non-limiting embodiments, device 100 may further include a film 117 removably attached to applicator 120. Film 117 may be formed of any suitable material, and may be configured to adhere to an outer portion of enclosure 118 and/or distal end 114 of container 110, to maintain a fluid tight and, optionally, air-tight seal between applicator 120 and the external environment. Film 117 may be peelable, and thus may include an adhesive or mechanical bonding on at least one side thereof (e.g., a side facing enclosure 118 and/or distal end 114 of container 110).

Turning to FIGS. 3A-4C, shown are non-limiting embodiments of enclosure 118 and/or distal end 114 of container 110, showing various configurations of opening(s) 119 that may be formed in a proximal end of enclosure 118 and/or distal end 114 of container 110 to place applicator 120 in fluid communication with interior 130 of container 110. Opening(s) 119 may be arranged in any suitable manner, and the embodiments illustrated in the accompanying figures are not limiting. However, opening(s) 119 may be arranged as one or more circular openings (e.g., FIGS. 3A and 4A), one or more radially-extending slots (e.g., FIGS. 4B and 4C), optionally where a plurality of slots extend radially from a single central point (e.g., FIG. 4B), and/or may form a particular shape, such as a cross (e.g., FIG. 4C), and/or one or more opening(s) 119 may be one or more axially-extending slots (e.g., FIG. 4D).

Figure 5A:
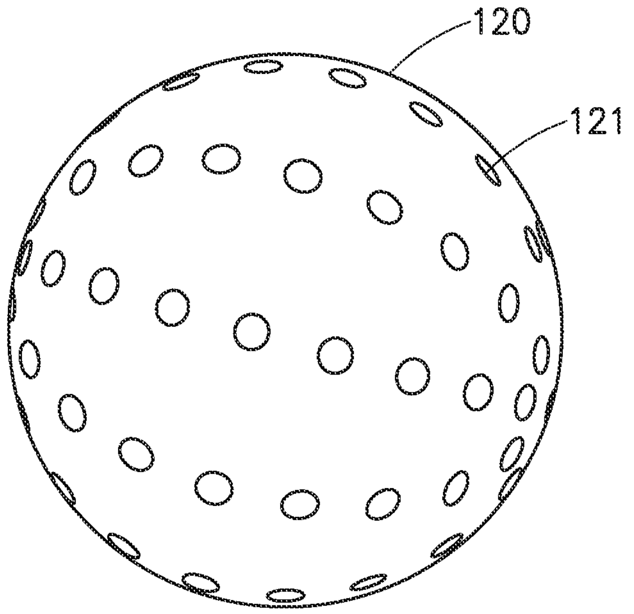
FIG. 5A is a partial view of skin preparation devices according to non-limiting embodiments described herein.
Figure 5B:
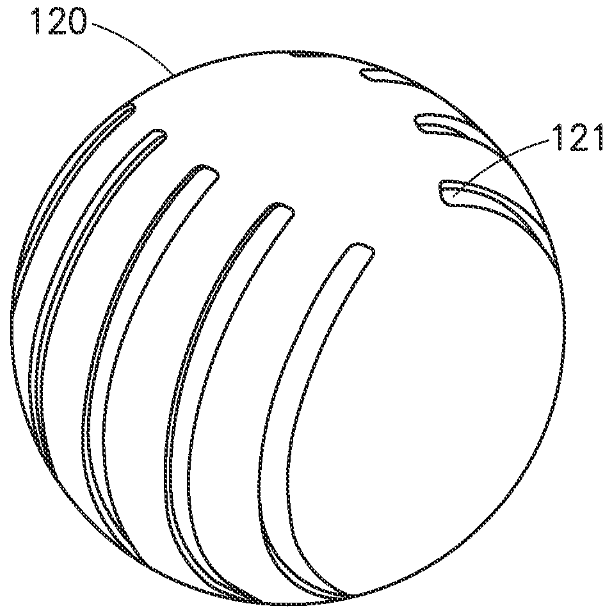
FIG. 5B is a partial view of skin preparation devices according to non-limiting embodiments described herein.

Turning to FIGS. 5A and 5B, as noted previously, in non-limiting embodiments, applicator 120 may be a spherical member that is rotatable within enclosure 118 and/or distal end 114 of container 110. In non-limiting embodiments, such a spherical member may include one or more indentations on an outer surface thereof. Such indentations may assume any useful size and shape, but in non-limiting embodiments may be circular (e.g., FIG. 5A) and or elongated (e.g., FIG. 5B).

Figure 7:
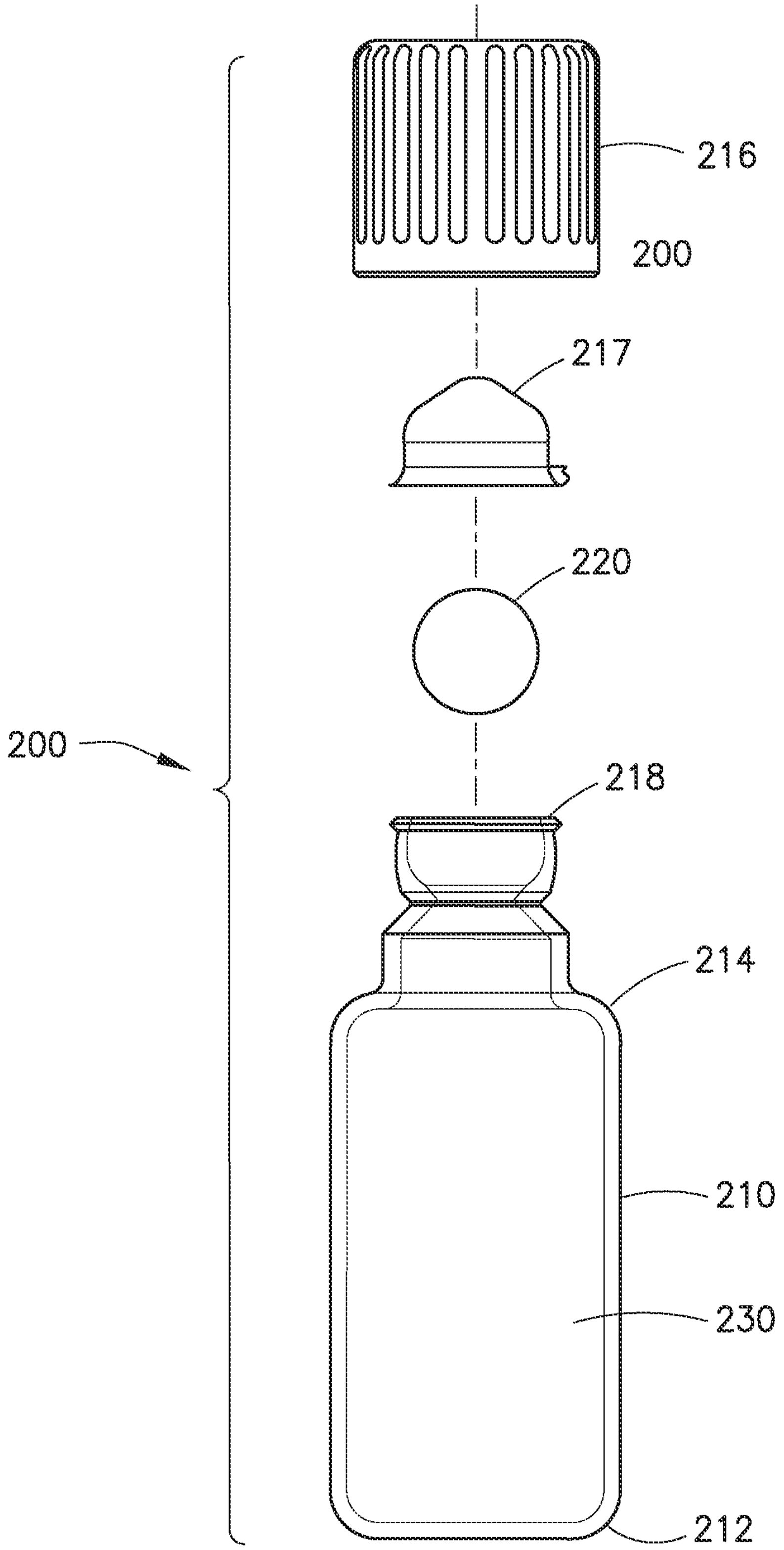
FIG. 7 is an exploded view of a skin preparation device according to non-limiting embodiments described herein.
Figure 8B:
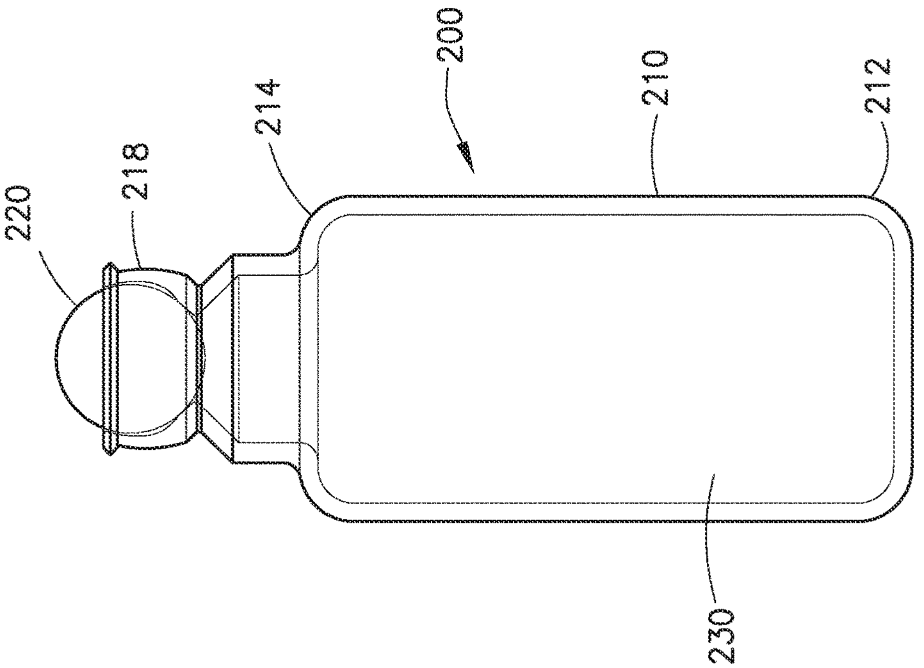
FIG. 8B is a side view of a skin preparation device according to non-limiting embodiments described herein.
Figure 8A:
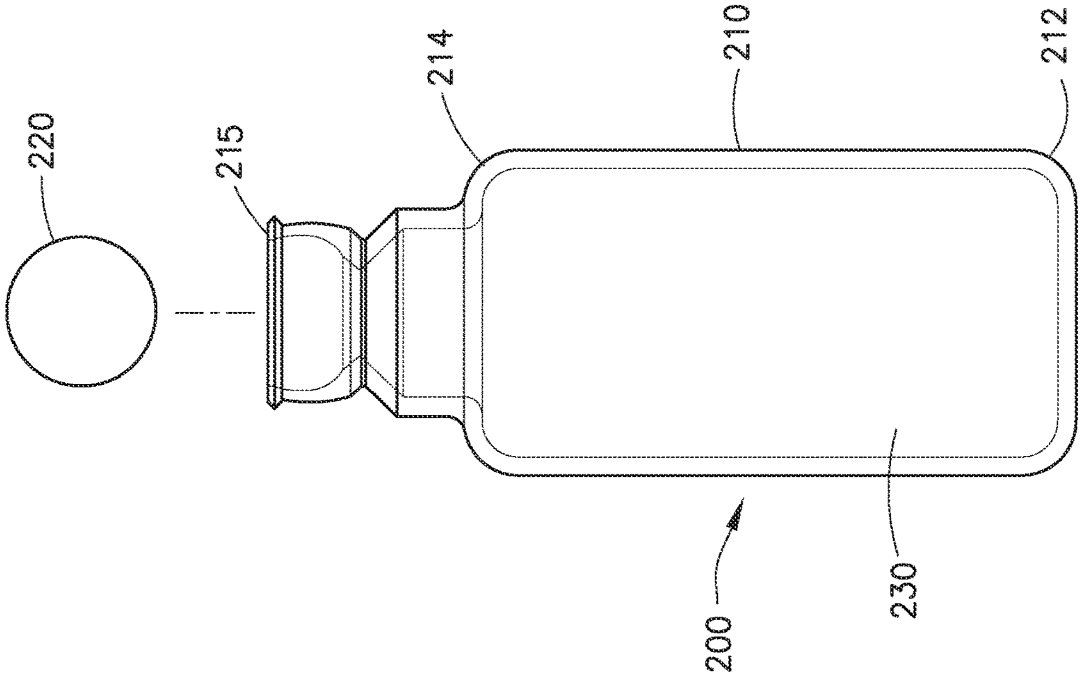
FIG. 8A is a side view of a skin preparation device according to non-limiting embodiments described herein.

Turning to FIGS. 7-8B, shown is a non-limiting embodiment of device 200, including container 210, having proximal end 212 and distal end 214, defining an interior 230 configured to hold a liquid, such as a disinfecting solution. Device 200 may also include an enclosure 218 configured to hold applicator 220. Device 200 may further include removable film 217 and cap 216, as described previously. In the non-limiting embodiment of device 200 shown in FIGS. 7 and 8, enclosure 218 is in the form of a cup that holds applicator 220 and allows applicator 220 to freely rotate, rather than a cylindrical structure with a frustoconical distal portion. As can be appreciated from a comparison of FIGS. 3, 8A, and 8B, enclosure 218 differs from enclosure 118 in that a flange 215 holds applicator 220 in place within enclosure 218 in the embodiment of FIGS. 7 and 8A-8B, while applicator 120 is held within enclosure 118 by the narrowing of the distal end of enclosure 118 in the embodiment of FIG. 3.

Turning to FIGS. 9-15B, shown is a non-limiting embodiment of device 300, including container 310, having proximal end 312 and distal end 314, defining an interior 330 configured to hold a liquid, such as a disinfecting solution. Device 300 may also include an enclosure 318 configured to hold applicator 321, and a removable film 317 and cap 316 overlaying applicator 321. In the non-limiting embodiment of applicator 321 shown in FIGS. 9-15B, applicator 321 may be a porous material, such as a foam and/or a sponge material, that can be used to both apply disinfecting solution from interior 330 of container 310 and to scrub and/or abrade the patient's skin, which may provide greater disinfection. Applicator 321 may assume any useful shape and be formed of any useful material, though as noted above, porous materials, optionally those that may be abrasive, are embodied in FIGS. 9-15B.

With regard to the embodiments of FIGS. 9-15B, in non-limiting embodiments, for example as shown in FIGS. 11A-13E, device 300 may include container 310, having proximal end 312 and distal end 314, defining an interior 330 configured to hold a liquid, such as a disinfecting solution. Device 300 may also include an enclosure 318 configured to hold applicator 321, a removable film 317 and cap 316 overlaying applicator 321, and a pin 350. Pin 350 may include a proximal end 352, distal end 354, tip 356, a sealing portion 360, and one or more ribs 358 arranged between proximal end 352 and distal end 354 (e.g., FIG. 11A). Tip 356 may include, in non-limiting embodiments, a radially-outwardly-extending flange defining a circumference, with one or more openings in the flange (e.g., FIG. 11B). Tip 356 may, in non-limiting embodiments, be rounded. One or more ribs 358 may define one or more openings 359 between proximal end 352 and distal end 354. Pin 350 may be snap or friction fit within enclosure 318. Pin 350 may be formed of any suitable material or mixtures of materials. For example, tip 356 of pin may be formed of a flexible or rigid material, sealing portion 360 may be formed of a rubber material, or other material that can form a fluid tight seal, and one or more ribs 358 may be formed of a flexible material, optionally a resiliently-flexible material such that pin 350 may be compressed longitudinally by application of a force to, for example, tip 356 (as shown in FIG. 13C-13D), and may return to an original configuration (as shown in, for example, FIGS. 13A-13B) when the force is removed. In non-limiting embodiments, sealing portion is a separate rubber ring that is received about a circumference of pin 350.

Figure 13B:
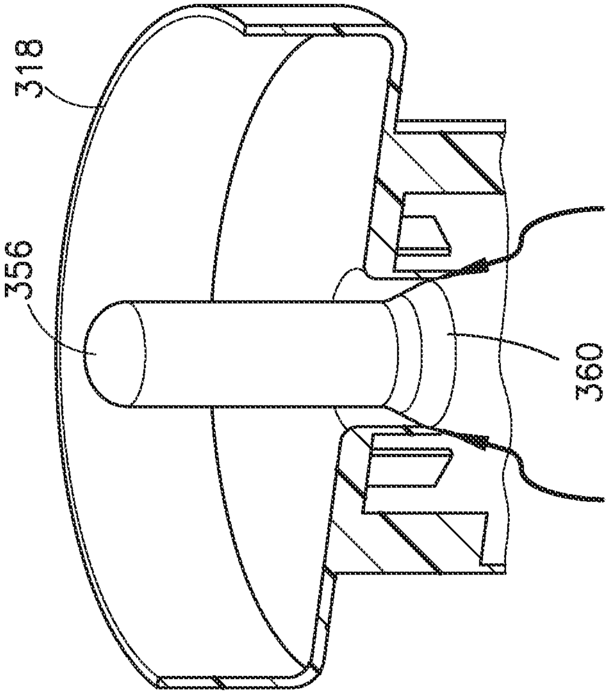
FIG. 13B is a partial view of a skin preparation device according to non-limiting embodiments described herein.
Figure 13A:
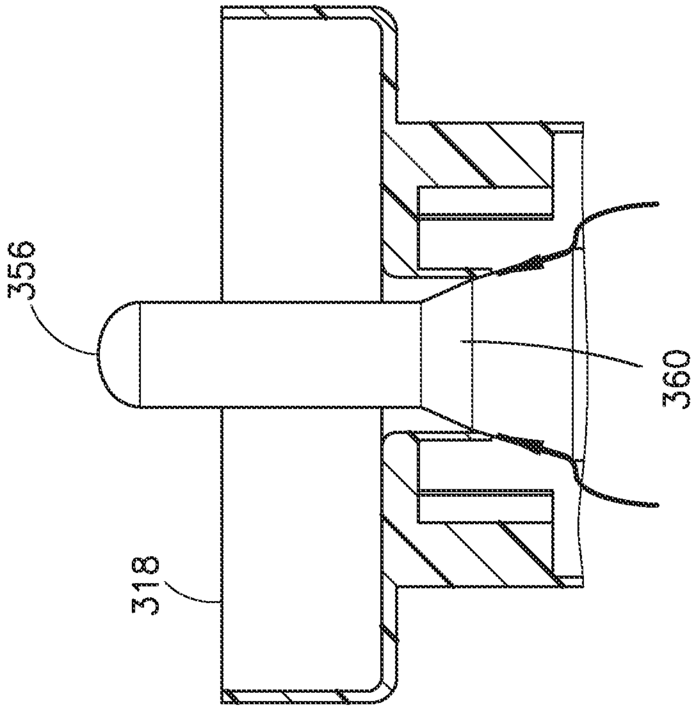
FIG. 13A is a partial view of a skin preparation device according to non-limiting embodiments described herein.
Figure 13D:
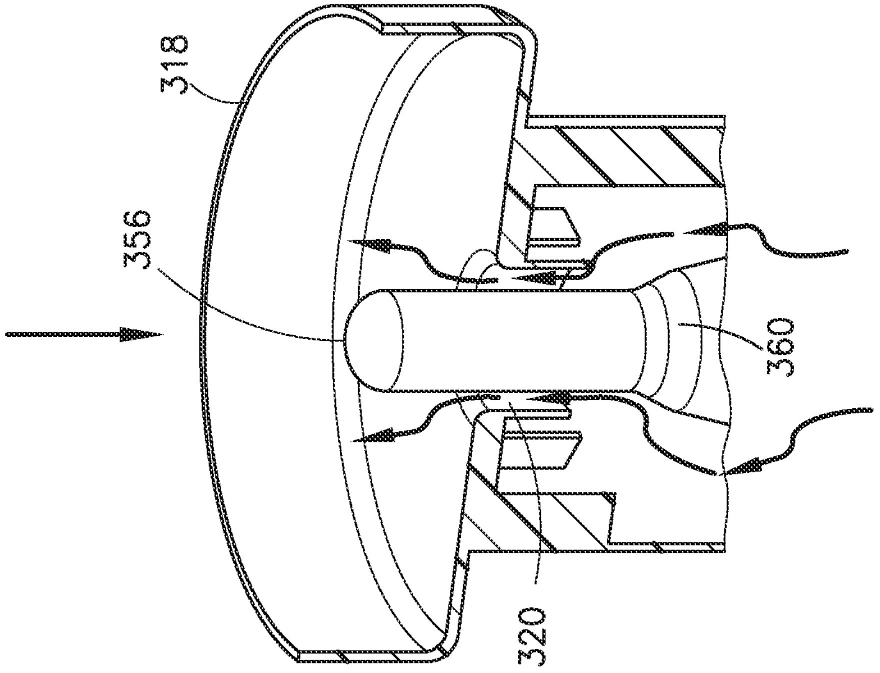
FIG. 13D is a partial view of a skin preparation device according to non-limiting embodiments described herein.
Figure 13C:
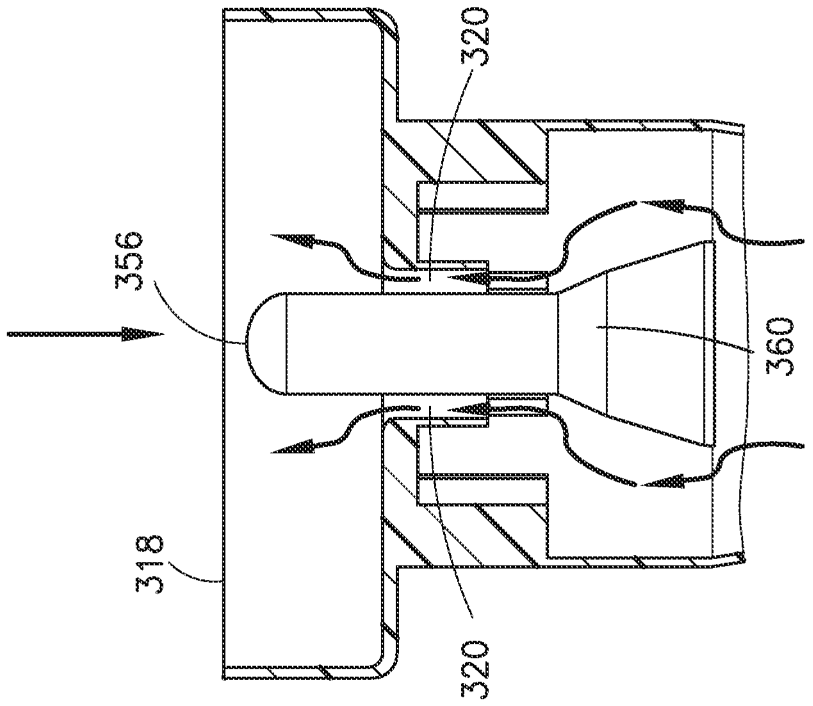
FIG. 13C is a partial view of a skin preparation device according to non-limiting embodiments described herein.
Figure 13E:
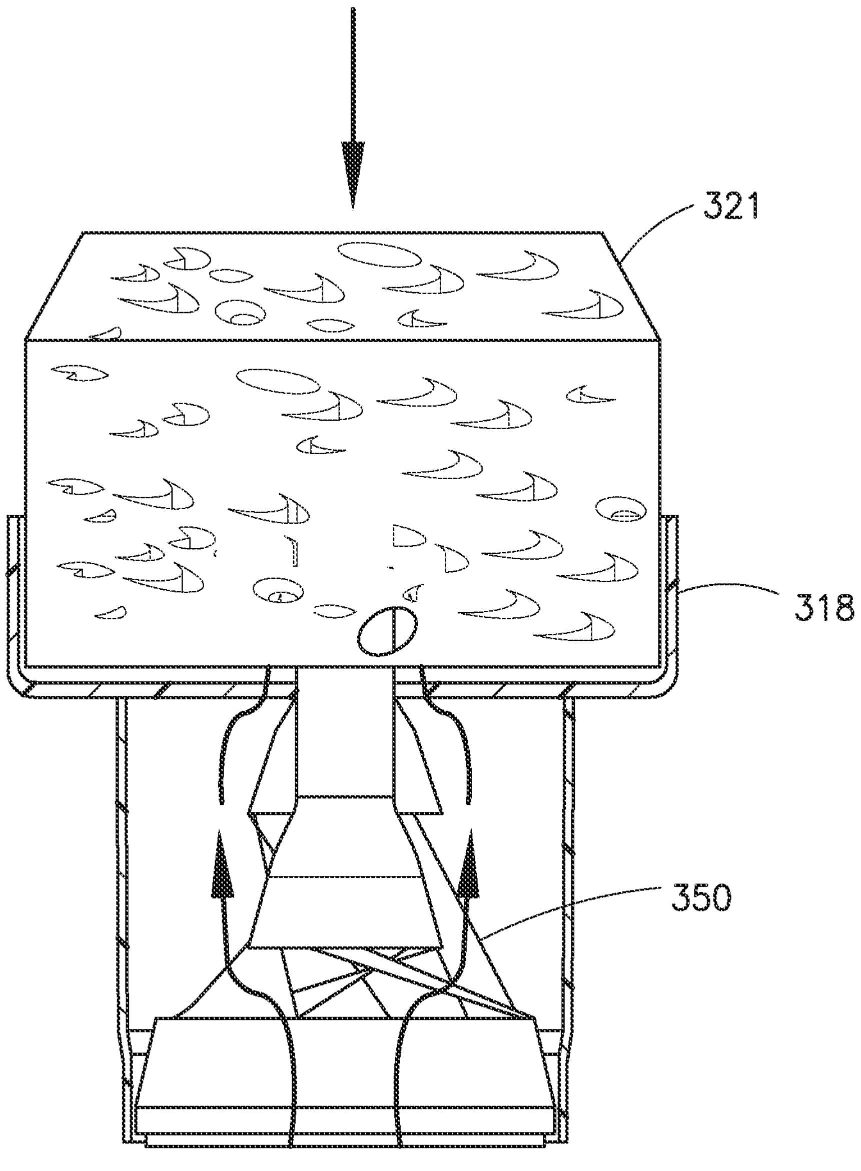
FIG. 13E is a partial view of a skin preparation device according to non-limiting embodiments described herein.

With reference to FIGS. 13A-13B, in an original configuration, pin is received within an opening in enclosure 318, in such a way that pin 350 and sealing portion 360 prevent flow of disinfecting solution from container interior 330, through enclosure 318, and to applicator 321, by engagement between scaling portion 360 an inner portion 322 of enclosure 318. Turning to FIGS. 13C-13E, when device 300 is to be used to apply disinfecting solution to a patient's skin, device 300 is pressed against the skin, which applies a force to tip 356 of pin 350. This force causes a compression of one or more ribs 358, which moves sealing portion out of engagement with interior 322 of enclosure 318, allowing disinfecting solution to pass between pin 350 and interior 322.

Figure 14:
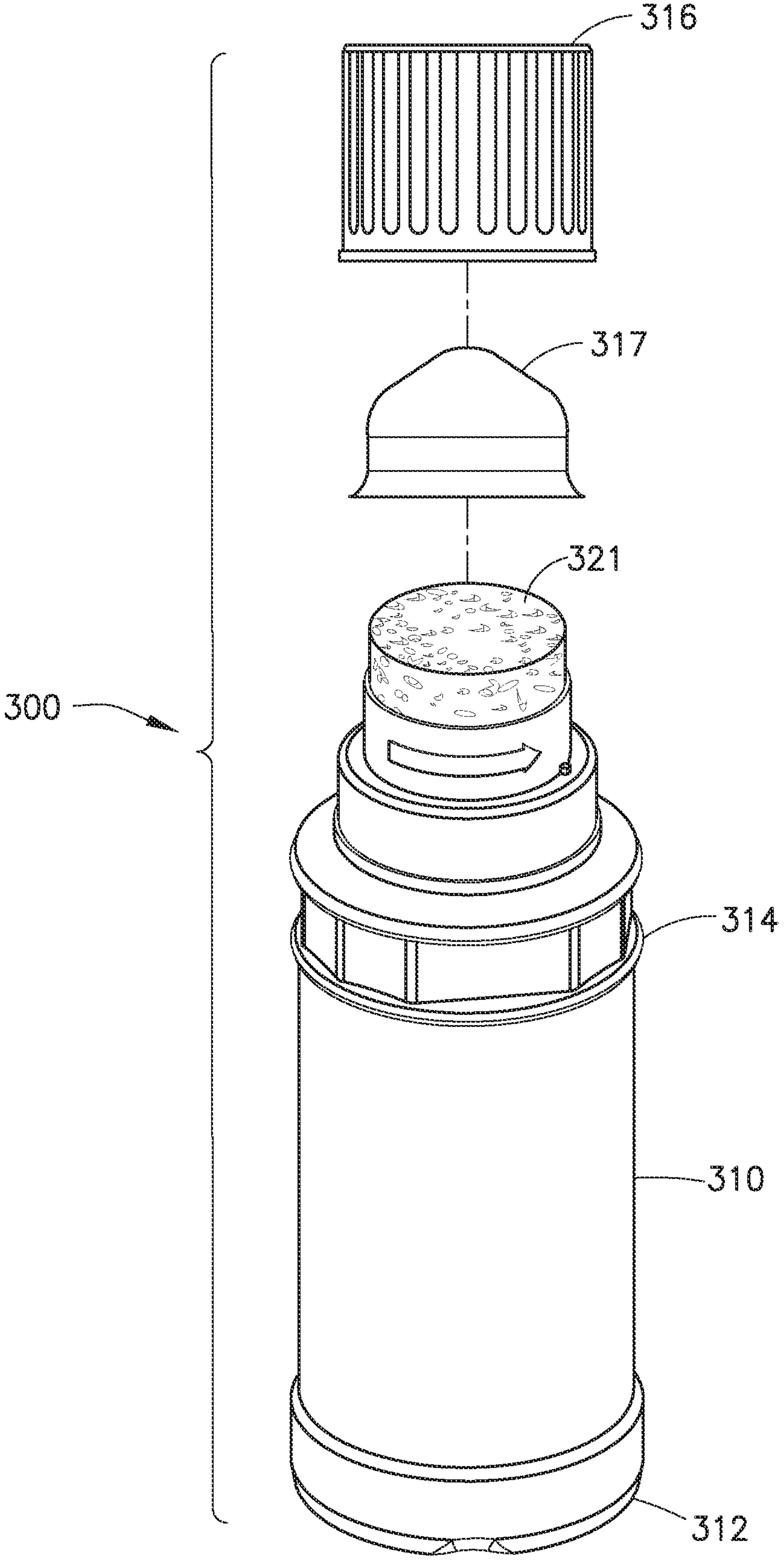
FIG. 14 is an exploded view of a skin preparation device according to non-limiting embodiments described herein.
Figure 15A:
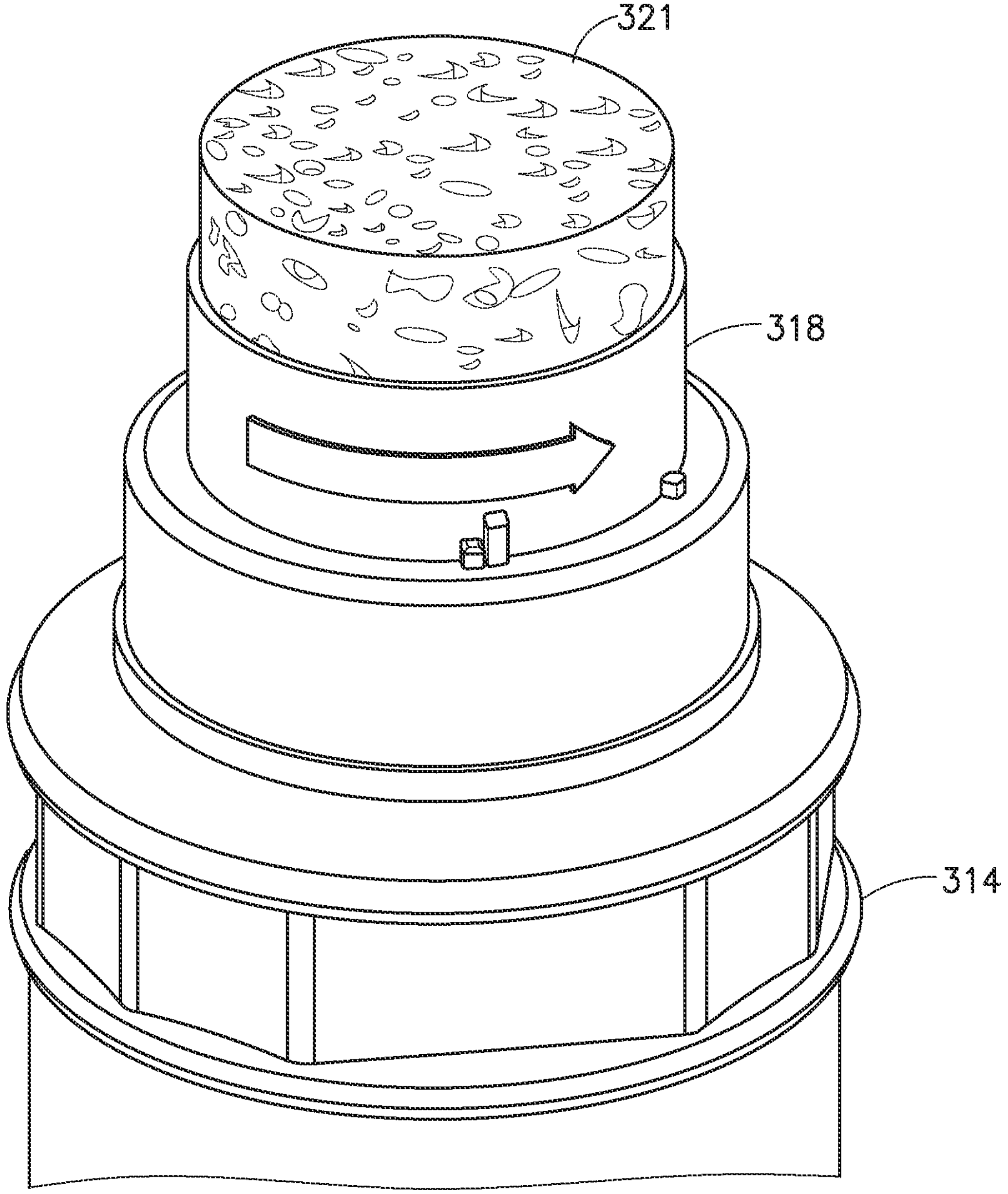
FIG. 15A is a partial side view of a skin preparation device according to non-limiting embodiments described herein.
Figure 15B:
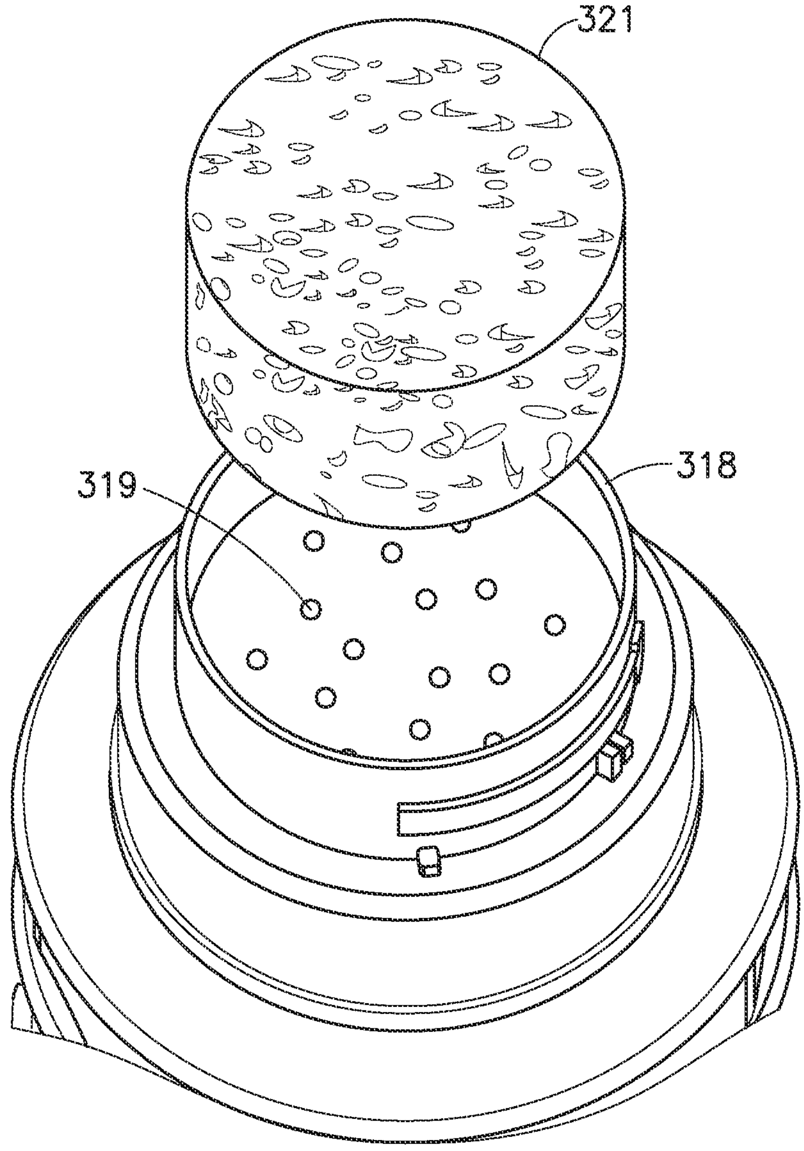
FIG. 15B is an exploded view of a skin preparation device according to non-limiting embodiments described herein.

Turning to FIGS. 14-15B, in non-limiting embodiments, enclosure 318 and/or distal end 314 of container 310 may be rotatable relative to container 310 in a number of configurations. In a first configuration, for example, opening(s) 319 may be closed, such that applicator 321 is not in fluid communication with interior 330 of container 310. In a second configuration, optionally 90 degrees offset from the first configuration, one or more opening(s) 319, but not all, may be aligned with one or more corresponding openings in container 310, such that applicator 321 is partially in fluid communication with interior 330 of container 310 and some amount of disinfecting solution may be dispensed. In a third configuration, each of opening(s) 319 may be aligned with one or more corresponding openings in container 310, such that a greater amount of disinfecting solution may be dispensed.

Figure 16:
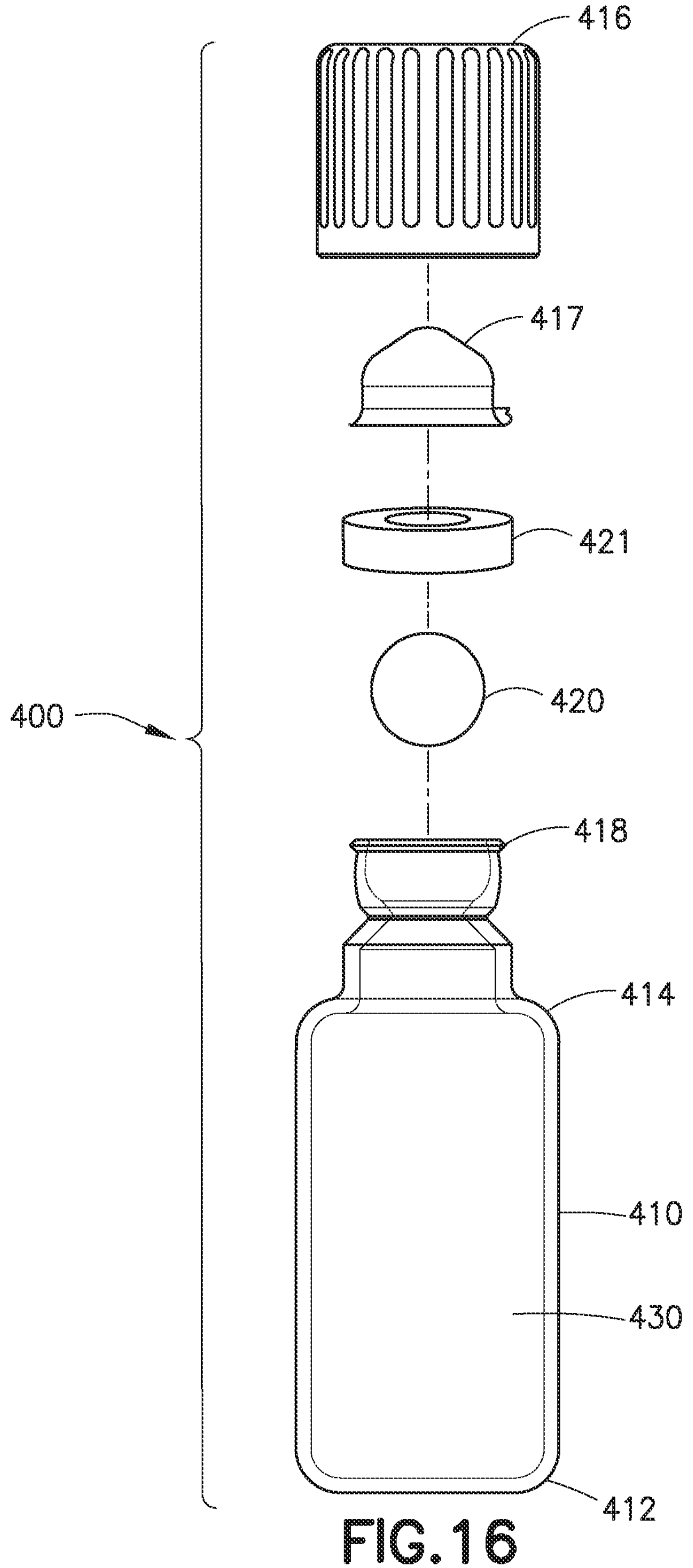
FIG. 16 shows an exploded perspective view of a skin preparation device according to non-limiting embodiments described herein.
Figure 17A:
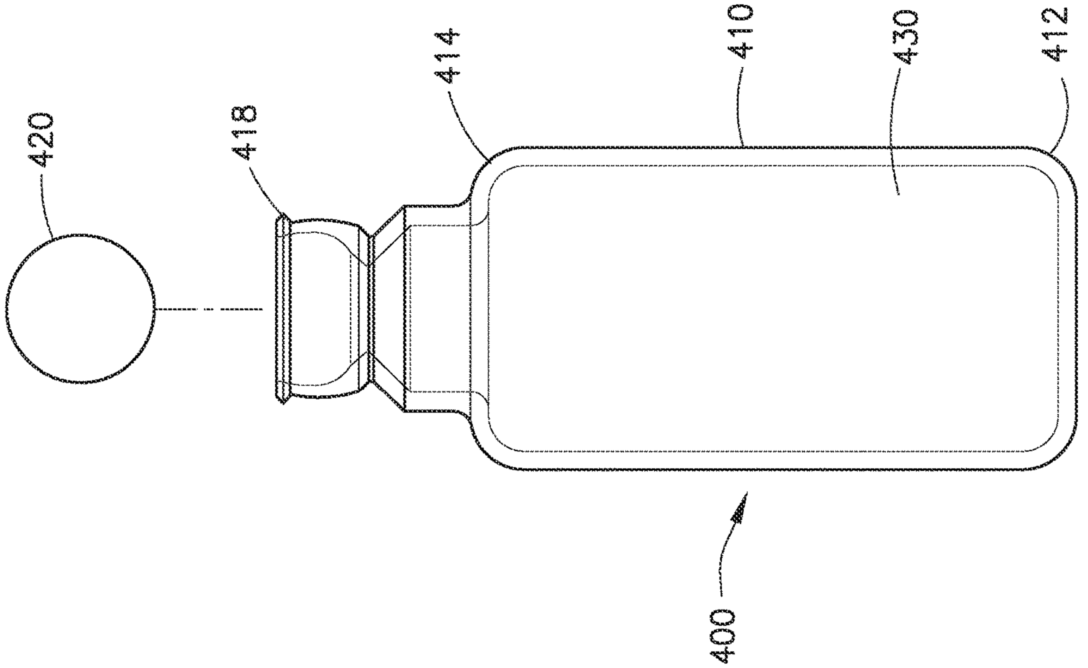
FIG. 17A is a side view of a skin preparation device according to non-limiting embodiments described herein.
Figure 17B:
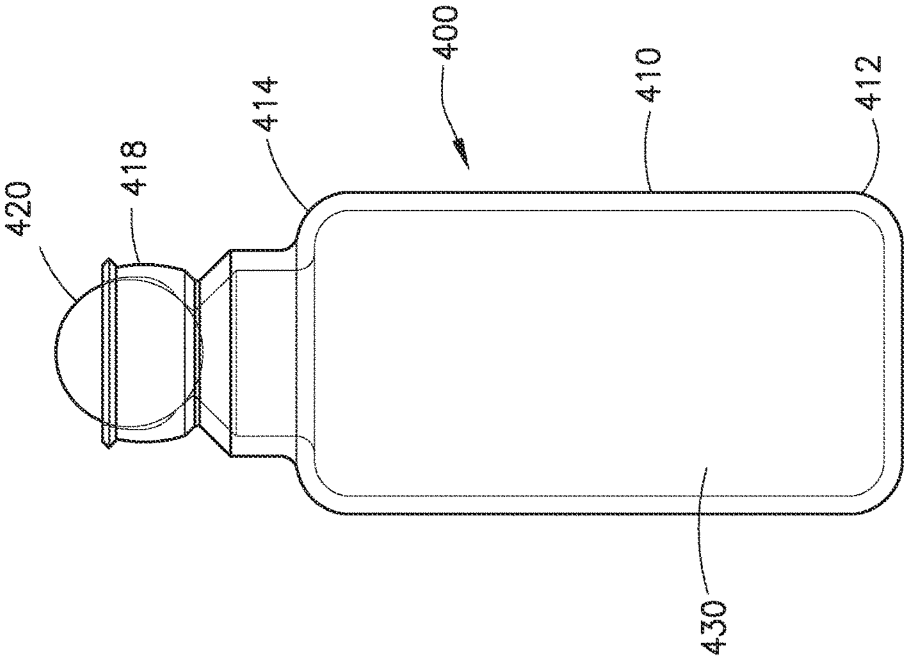
FIG. 17B is a side view of a skin preparation device according to non-limiting embodiments described herein.
Figure 18:
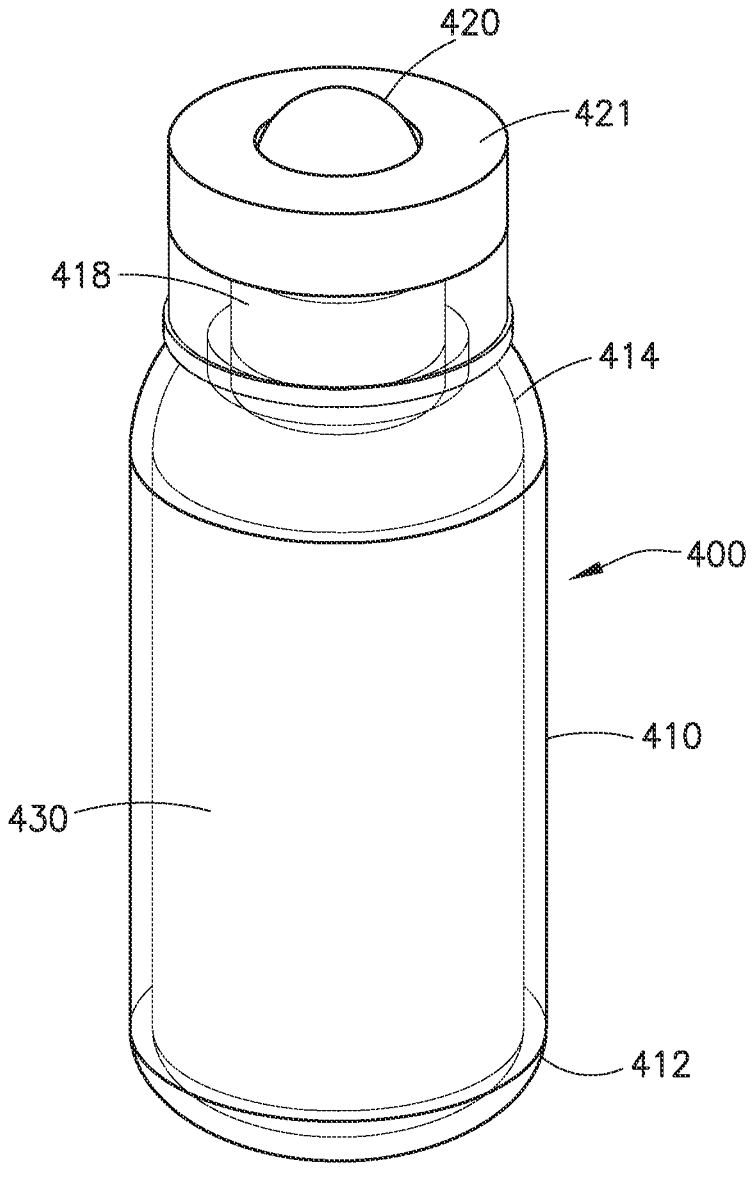
FIG. 18 is a perspective view of a skin preparation device according to non-limiting embodiments described herein.

Turning to FIGS. 16-18, shown is a non-limiting embodiment of device 400, including container 410, having proximal end 412 and distal end 414, defining an interior 430 configured to hold a liquid, such as a disinfecting solution. Device 400 may also include an enclosure 418 configured to hold applicator 420, 421 and a removable film 417 and cap 416 overlaying applicator 420, 421. As shown in the non-limiting embodiment of FIG. 16, applicator 420, 421 is a combination of applicators, including a spherical (e.g., roller) applicator 420, as described above, and a porous applicator 421, also as described above. For example, porous applicator 421 may be in the form of a ring, with a circumference defining an opening in which spherical applicator 420 is received.

Figure 19A:
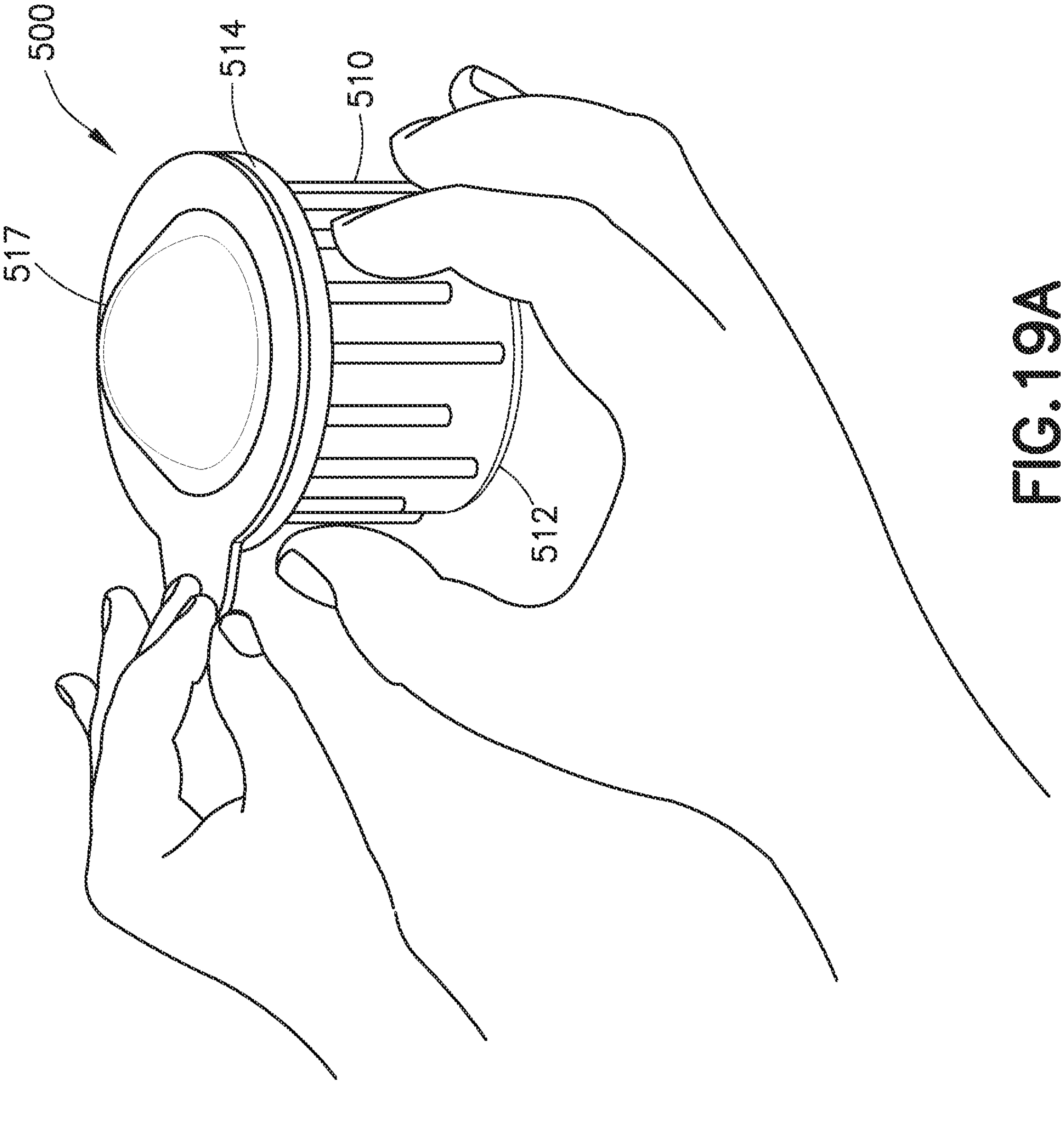
FIG. 19A is a side view of a skin preparation device according to non-limiting embodiments described herein.
Figure 19B:
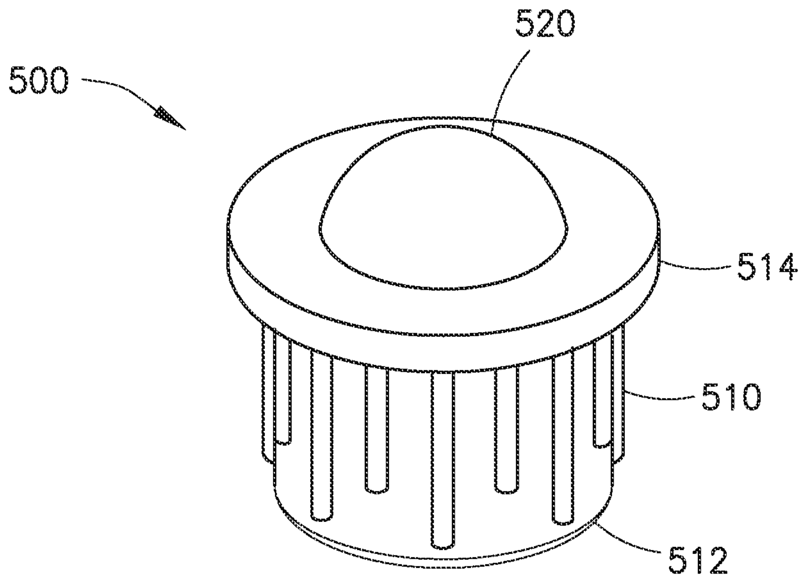
FIG. 19B is a side view of a skin preparation device according to non-limiting embodiments described herein.
Figure 19C:
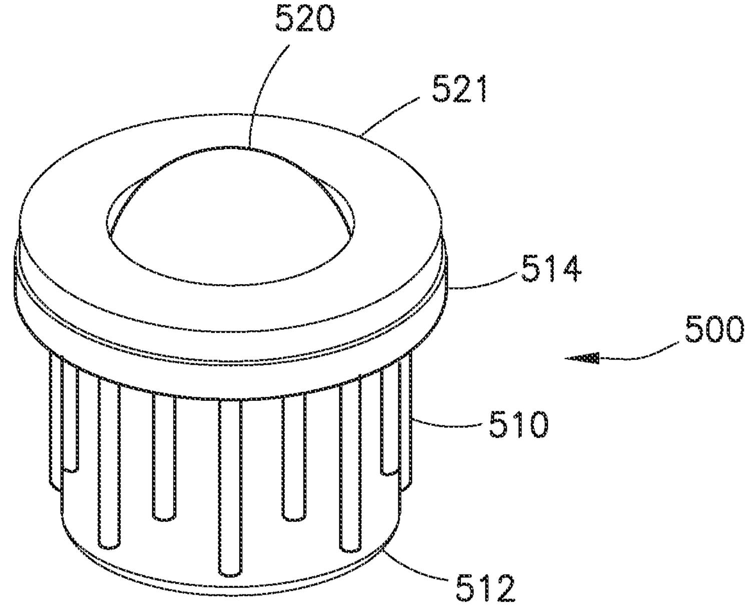
FIG. 19C is a side view of a skin preparation device according to non-limiting embodiments described herein.
Figure 20:
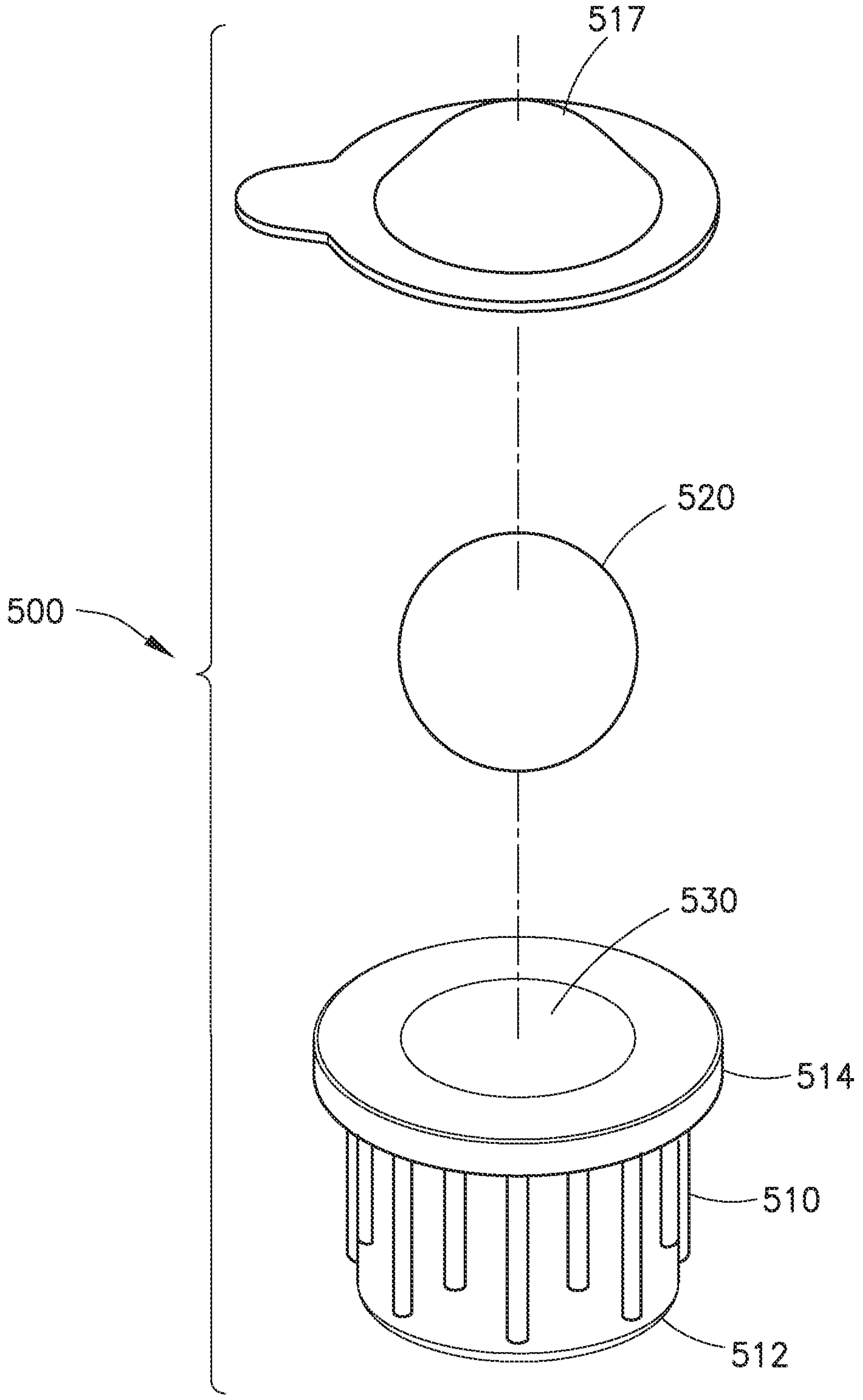
FIG. 20 is an exploded view of a skin preparation device according to non-limiting embodiments described herein.
Figure 21:
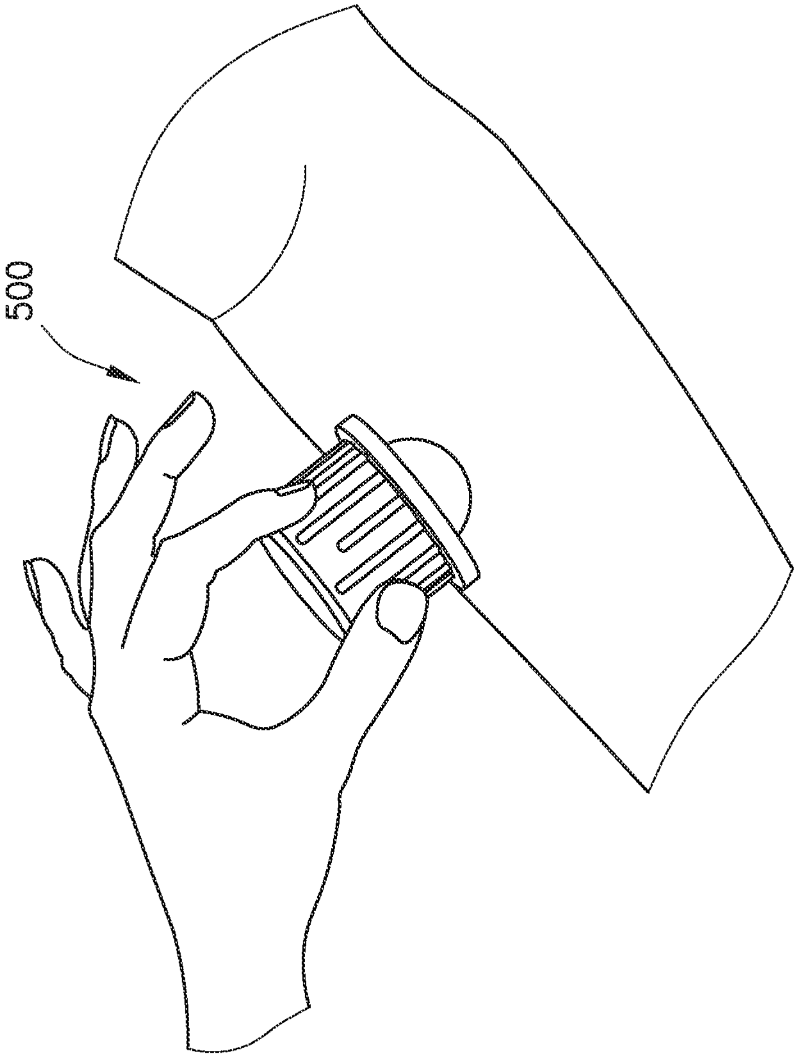
FIG. 21 is a use view of a skin preparation device according to non-limiting embodiments described herein.
Figure 22B:
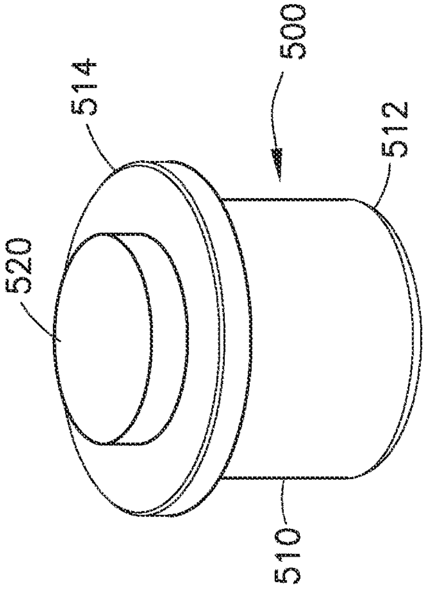
FIG. 22B is a side view of a device and system for skin preparation according to non-limiting embodiments described herein.
Figure 22C:
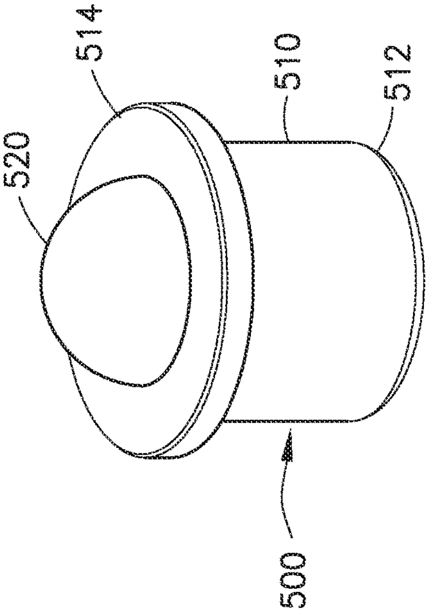
FIG. 22C is a side view of a device and system for skin preparation according to non-limiting embodiments described herein.
Figure 22A:
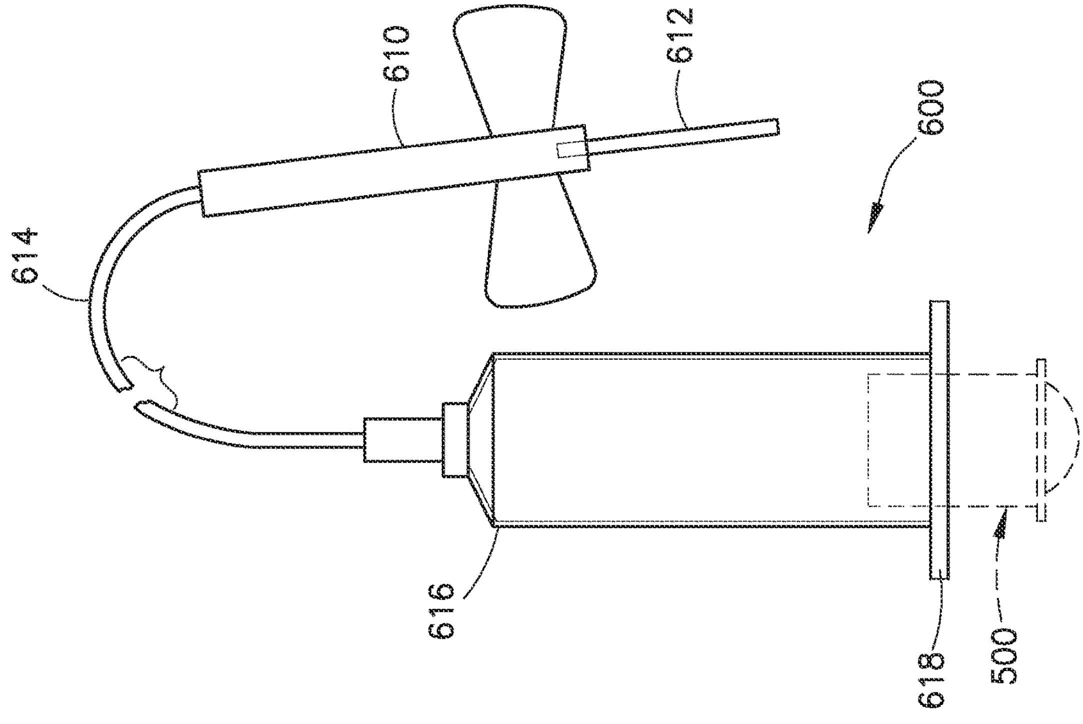
FIG. 22A is a side view of a device and system for skin preparation according to non-limiting embodiments described herein.

Turning to FIGS. 19A-20, shown is a non-limiting embodiment of device 500, including container 510, having proximal end 512 and distal end 514, defining an interior 530 configured to hold a liquid, such as a disinfecting solution. Device 500 may also include an applicator 520 and a removable film 517 overlaying applicator 520. Device 500 may also include, in non-limiting embodiments and for example as shown in FIG. 19C, an applicator 520, 521, e.g., a combination of applicators, including a spherical (e.g., roller) applicator 520, as described above, and a porous applicator 521, also as described above. In non-limiting embodiments, container 510 may be of a significantly smaller size than other containers in other embodiments described herein, making container 510 suitable for inclusion in a kit with other medical devices, as will be described below. In non-limiting embodiments, container 510 includes, at distal end 514 thereof, a flange 515, which may be similar to flange 215 seen in the enclosure in the embodiment of FIGS. 7 and 8, and may serve to keep applicator 520 at least partially within container 510. A device, such as the devices described herein, but, with particular focus on the device 500 of FIGS. 19A-20, may be used to apply a disinfecting solution to a patient's skin, for example as shown in FIG. 21.

Turning to FIGS. 22A-23C, shown are non-limiting embodiments of kits including a skin preparation device as described herein. With regard to FIGS. 22A-22B, device 500 may include container 510, having proximal end 512 and distal end 514, defining an interior (not shown) configured to hold a liquid, such as a disinfecting solution. Device 500 may also include an applicator 520, which may be a spherical member (e.g., a roller applicator) and/or a porous applicator (e.g., a sponge applicator). Device 500 may include a removable film (not shown) overlaying applicator 520. A kit (FIG. 22A) may also include a blood collection set 600, which may include a catheter adapter 610, including a catheter 612 in fluid communication with a fluid conduit 614. Fluid conduit 614 may further be in fluid communication with a blood collection device holder 616. Suitable blood collection sets 600 and various components thereof are available commercially from, for example, Becton, Dickinson and Company (Franklin Lakes, NJ), under the names VACUTAINER®, ECLIPSE™, and SAFETY-LOK™. Blood collection device holder 616 may include one or more features 618 that allow skin preparation device 500 to be received. For example, device 500 may be received through a friction fit and/or a snap fit within at least a portion of the interior of blood collection device holder 616, as shown by the highlighting in FIG. 18A.

Figure 23B:
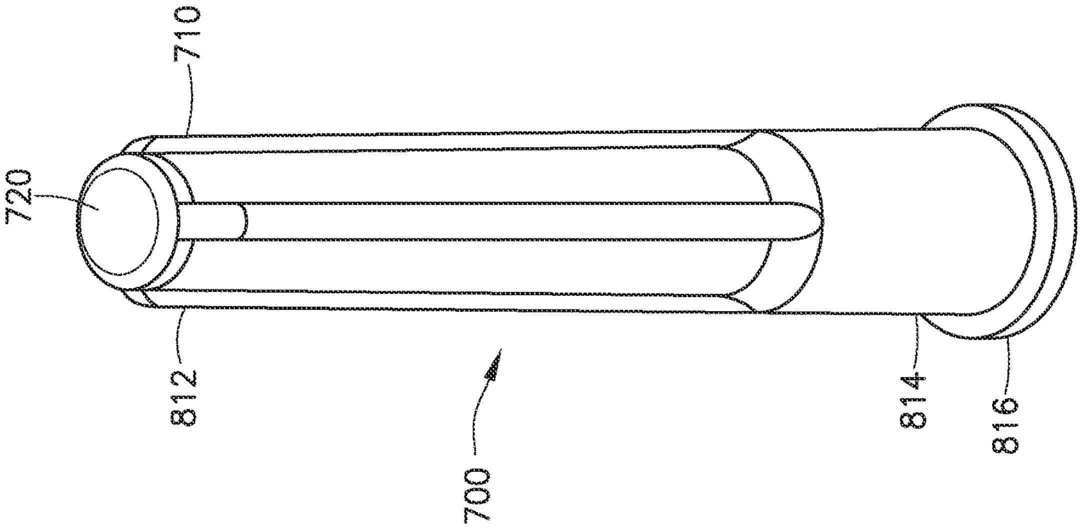
FIG. 23B is a side view of a skin preparation device according to non-limiting embodiments described herein.
Figure 23A:
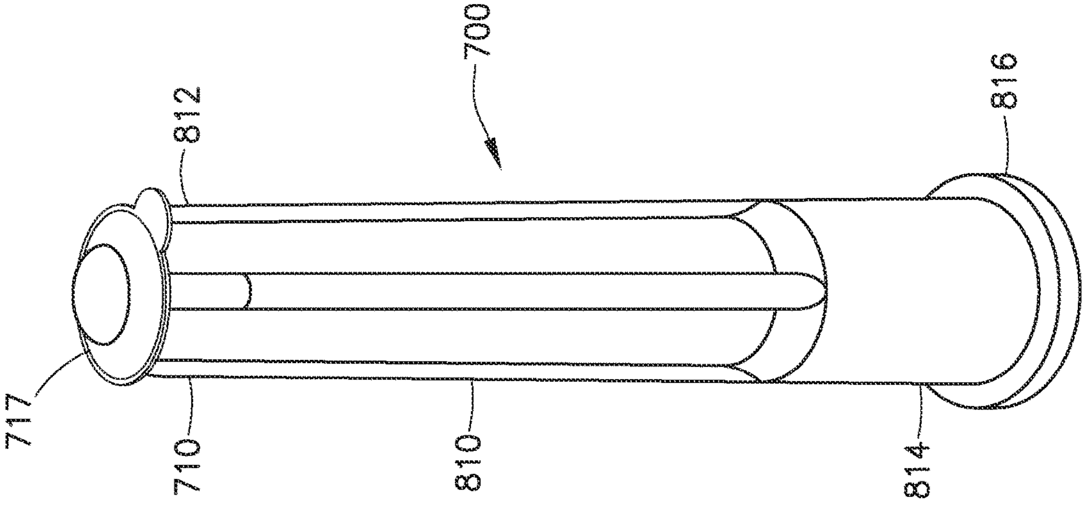
FIG. 23A is a side view of a skin preparation device according to non-limiting embodiments described herein.
Figure 23C:
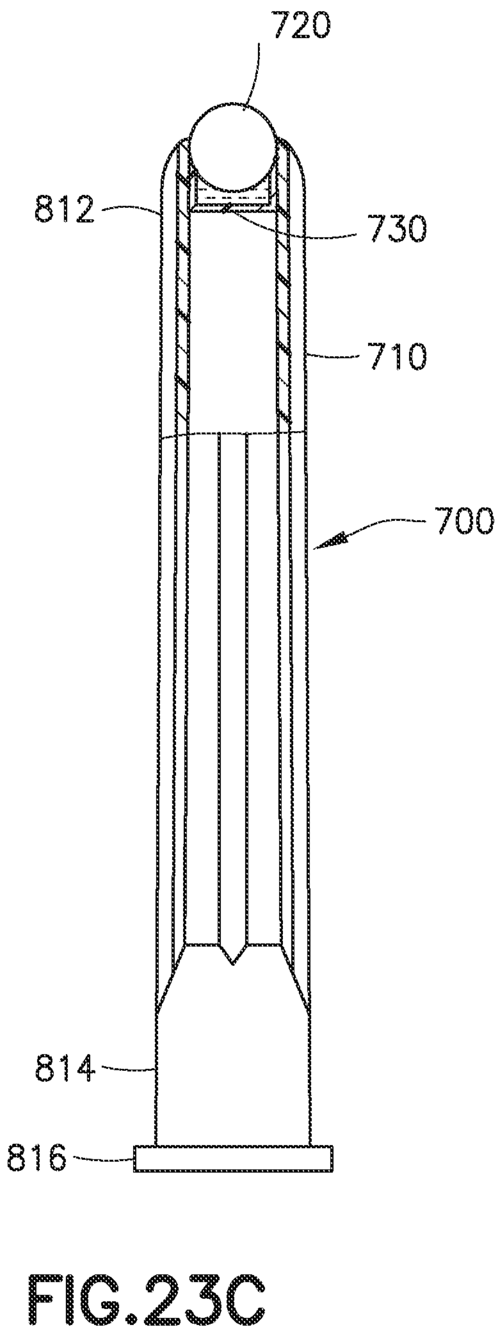
FIG. 23C is a side view of a skin preparation device according to non-limiting embodiments described herein.

With regard to FIGS. 23A-23C, shown is a non-limiting embodiment of a drug delivery device 700 with a skin preparation device incorporated therein. Drug delivery device 700 may generally include a housing 810, having a proximal end 812 and distal end 814, defining an interior holding a syringe (not shown). Drug delivery device 700 may include a needle cover 816 that is displaceable relative to the distal end 814 of housing 810 for delivering an injection and protecting a user from the needle (not shown) before and following drug delivery. Skin preparation device may include a container 710, which may be part of delivery device housing 810, and a removable film 717 overlaying an applicator 720, which, as described herein, may be a spherical member (e.g., a roller applicator) or a porous applicator (e.g., a sponge applicator). Skin preparation device 500 may be received within housing 810 of drug delivery device 700 at proximal end 812 thereof.

Although the present disclosure has been described in detail for the purpose of illustration based on what is currently considered to be the most practical and preferred embodiments or aspects, it is to be understood that such detail is solely for that purpose and that the present disclosure is not limited to the disclosed embodiments or aspects, but, on the contrary, is intended to cover modifications and equivalent arrangements that are within the spirit and scope of the appended claims. For example, it is to be understood that the present disclosure contemplates that, to the extent possible, one or more features of any embodiment may be combined with one or more features of any other embodiment.

The invention claimed is:

1. A skin preparation device, comprising:

a container having a proximal end, a distal end, and a sidewall therebetween defining an interior, the distal end of the container including an enclosure having an open distal end and a flexible web at a proximal end thereof;

a disinfecting solution received within the interior;

an axially displaceable roller applicator comprising a spherical member received rotatably within the enclosure in fluid communication with the interior of the container and at least a portion of the spherical member extends distally beyond the enclosure, the spherical member held within the enclosure by an inwardly-extending flange, the enclosure comprising one or more openings in the proximal end thereof, the one or more openings placing the spherical member in fluid communication with the interior of the container;

a removable film arranged on an outer surface of the skin preparation device configured to provide fluid tight seal between the axially displaceable roller applicator and an external environment; and a cap removably attached to the distal end of the container overlaying the removable film, wherein the flexible web is resilient and can flex when a user applies pressure to the axially displaceable roller applicator and the flexible web is configured to return to an original position when a force is removed from the displaceable roller;

wherein the one or more openings comprise a plurality of circular openings.

2. The skin preparation device of claim 1, wherein the axially displaceable roller applicator comprises a porous material.

3. The skin preparation device of claim 2, further comprising:

a ring of a porous material defining a central opening and arranged circumferentially about the distal end of the container; and the axially displaceable roller applicator received in the central opening of the porous material.

4. The skin preparation device of claim 1, wherein the enclosure is a cylindrical enclosure having a frustoconical distal end.

5. The skin preparation device of claim 1, wherein the one or more openings comprise a plurality of circular openings.

6. A skin preparation device, comprising:

a container having a proximal end, a distal end, and a sidewall therebetween defining an interior, the distal end of the container including an enclosure having an open distal end and a flexible web at a proximal end thereof;

a disinfecting solution received within the interior;

an axially displaceable roller applicator comprising a spherical member received rotatably within the enclosure in fluid communication with the interior of the container and at least a portion of the spherical member extends distally beyond the enclosure, the spherical member held within the enclosure by an inwardly-extending flange, the enclosure comprising one or more openings in the proximal end thereof, the one or more openings placing the spherical member in fluid communication with the interior of the container;

a removable film arranged on an outer surface of the skin preparation device configured to provide fluid tight seal between the axially displaceable roller applicator and an external environment; and a cap removably attached to the distal end of the container overlaying the removable film, wherein the flexible web is resilient and can flex when a user applies pressure to the axially displaceable roller applicator and the flexible web is configured to return to an original position when a force is removed from the displaceable roller, wherein the one or more openings comprise a plurality of elongated slots.

7. The skin preparation device of claim 6, wherein the plurality of elongated slots are arranged in a radially-extending pattern from a center of the proximal end of the enclosure to an outer edge of the proximal end of the enclosure.

8. The skin preparation device of claim 6, wherein the plurality of elongated slots intersect at a center of the proximal end of the enclosure.

9. The skin preparation device of claim 6, wherein the plurality of elongated slots extend distally from a proximal end of the enclosure.

10. The skin preparation device of claim 1, wherein the axially displaceable roller applicator comprises the spherical member comprising one or more indentations in an outer surface thereof.

11. The skin preparation device of claim 10, wherein the one or more indentations comprise a plurality of circular indentations.

12. The skin preparation device of claim 10, wherein the one or more indentations comprise a plurality of elongated indentations.

13. The skin preparation device of claim 1, wherein the distal end of the container is rotatable between a first configuration, in which the axially displaceable roller applicator is not in fluid communication with the interior of the container, and a second configuration, in which the axially displaceable roller applicator is in fluid communication with the interior of the container.

14. The skin preparation device of claim 1, wherein the disinfecting solution comprises chlorhexidine gluconate (CHG).

15. The skin preparation device of claim 1, wherein the disinfecting solution comprises isopropyl alcohol (IPA).

16. The skin preparation device of claim 1, wherein the disinfecting solution comprises from 0.5% to 4% CHG and 70% IPA.

17. The skin preparation device of claim 1, wherein the disinfecting solution comprises 2% CHG and 70% IPA.

18. A kit comprising:

a blood collection device comprising:

a catheter assembly comprising a catheter and a fluid flow conduit in fluid communication with the catheter; and a blood collection device holder; and a skin preparation device according to claim 1.

19. A kit comprising:

a blood collection device comprising:

a catheter assembly comprising a catheter and a fluid flow conduit in fluid communication with the catheter; and a blood collection device holder; and a skin preparation device according to claim 6.

* * * * *